United States Patent [19] [11] 4,000,138
Snell et al. [45] Dec. 28, 1976

[54] ORGANIC COMPOUNDS AND COMPOSITIONS CONTAINING THEM

[75] Inventors: Brian Kenneth Snell; Richard Stewart Elias; Peter Frank Hilary Freeman, all of Bracknell, England

[73] Assignee: Imperial Chemical Industries Limited, London, England

[22] Filed: Jan. 21, 1976

[21] Appl. No.: 650,864

Related U.S. Application Data

[60] Division of Ser. No. 207,530, Dec. 13, 1971, which is a continuation-in-part of Ser. No. 741,254, July 1, 1968, abandoned, which is a continuation-in-part of Ser. No. 619,607, March 1, 1967, abandoned.

[30] Foreign Application Priority Data

Mar. 31, 1966 United Kingdom ............ 14271/66
June 30, 1967 United Kingdom ............ 30348/67
June 30, 1967 United Kingdom ............ 30354/67

[52] U.S. Cl. .................. 260/256.4 C; 424/251; 424/357

[51] Int. Cl.$^2$ ................................. C07D 239/00
[58] Field of Search ............................ 260/256.4 C

[56] References Cited

UNITED STATES PATENTS 2,610,185  9/1952  Oroshnik .................. 260/256.4
2,610,186  9/1952  Oroshnik .................. 260/256.4

FOREIGN PATENTS OR APPLICATIONS 245,623  7/1963  Australia
1,019,227  2/1966  United Kingdom

*Primary Examiner*—Dale R. Ore
*Attorney, Agent, or Firm*—Cushman, Darby & Cushman

[57] ABSTRACT

2-Ethylamino-4-methyl-5-n-butyl-6-hydroxypyrimidine and salts thereof which are useful in combating plant diseases.

1 Claim, No Drawings

ORGANIC COMPOUNDS AND COMPOSITIONS CONTAINING THEM

This application is a divisional of Ser. no. 207,530, filed Dec. 13, 1971, which application Ser. No. 207,530 is a continuation-in-part of Ser. No. 741,254, filed July 1, 1968, which in turn is a continuation-in-part of Ser. No. 619,607, filed Mar. 1, 1967 both now abandoned.

This invention relates to fungicidal compositions containing as an active ingredient a pyrimidine derivative, to new pyrimidine derivatives, to processes for making new pyrimidine derivatives and to methods for combating fungi, especially plant fungal diseases.

The survival of man has for a long time considerably depended upon his ability to protect crops from the various agents that tend to destroy them. With the rapidly increasing world population it becomes important that there be continuing improvements in the efficiency of the substances and methods using to provide crop protection. These improvements may reside, for example, in the form of more effective control of pests either by deploying less substance or labour. The substances and methods of this invention represent a major advance in both these directions.

It has been discovered that the application of certain pyrimidine derivatives by the methods of this invention considerably reduce, or even precludes damage to crops and other materials due to fungi. Fungus infections are destroyed or prevented from developing by the presence of one or more of the compounds, i.e. the compounds are fungicidal or fungistatic.

It has been found that, in general, pyrimidine derivatives (and their salts and ethers) which bear both a 2-amino substituent and a 6-hydroxy or 6-thiol group are active fungicides and that the fungicidal activity is widespread throughout a range of various other ring substituents. Certain combinations of additional substituents are particularly useful and some are more advantageous than others, as will be seen hereinafter. The present invention provides a process for combating plant fungi which comprises applying to the locus of a plant a fungicidally effective amount of a pyrimidine derivative of the general formula:

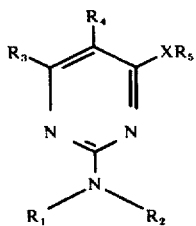

or a fungicidally effective amount of a salt thereof, wherein $R_1$ stands for hydrogen, lower alkyl, lower alkenyl, or phenyl-lower alkyl; $R_2$ is hydrogen, lower alkyl, lower alkenyl, lower alkyl phenyl, halophenyl, or lower alkoxycarbonyl-substituted phenyl, amino, anilino, cyano, lower alkylcarbonyl, halo-lower alkylcarbonyl, a nitrogen- containing monocyclic heterocyclic radical, phenyl-lower alkyl, lower alkyl substituted by a 6- membered heterocyclic nitrogen- containing radical, cycloalkyl, carbamoyl, or a nitro-substituted phenylsulphonyl group; or $R_1$ and $R_2$, together with the adjacent nitrogen atom, form a 5- or 6- membered heterocyclic ring which may contain one or more additional heterocyclic atoms, or form a guanidino or benzylidine- hydrazino group; $R_3$ is hydrogen, halogen, lower alkyl, lower alkylthio-lower alkyl, or unsubstituted or halo- or lower alkoxy-substituted phenyl; $R_4$ is hydrogen, halogen, lower alkyl, phenyl-lower alkyl, lower alkenyl, lower alkoxyalkyl, hydroxyhalo-lower alkyl, nitro, phenylazo, monocyclic hererocyclic substituted lower alkyl, phenyl, phenyloxy, or halo- or lower alkyl-substituted phenylthio, lower alkylsulphonyl, phenyl-lower alkylthio-, lower alkyl- or halo-substituted phenyl-lower alkyl, or a —CHO group; or $R_3$ and $R_4$ together form a lower alkylene or lower alkenylene bridging group; X is an atom of oxygen or sulphur; $R_5$ is hydrogen, hydroxy-lower alkyl, phenyl-lower alkyl, phenylcarbonyloxy lower alkyl, lower alkenyl, lower alkoxycarbonyl-lower alkyl, lower alkylcarbonyl-lower alkyl, di-lower alkylamino-lower alkyl, lower alkylthio-lower alkyl or lower alkoxy-lower alkyl; and a carrier for the active ingredient comprising a solid diluent, or a liquid diluent.

When $R_1$ is a lower alkyl or a lower alkenyl group it is preferably one comprising from 1 to 6 carbon atoms. The word "lower" as used in this specification and claims is intended to denote a group or radical containing from 1 to 6 carbon atoms. Thus, $R_1$, $R_2$, $R_3$, $R_4$ and $R_5$ may, for example, be methyl, ethyl, propyl, butyl, amyl, or hexyl, or they may, for example, be allyl, (crotyl, propenyl) or butenyl. Furthermore in the other substituents recited above for $R_1$ through $R_5$ the alkyl or alkenyl moieties, or indeed alkoxy, moieties, of, or incorporated in, these other substituents may equally be, for example, derived from methyl, ethyl, propyl, butyl, amyl or hexyl; or allyl, (crotyl) or butenyl, for example. Thus in the substituents referred, inter alia, to as:

lower alkoxy carbonyl-substituted phenyl
lower alkyl carbonyl
halo-lower alkyl carbonyl
phenyl lower alkyl
lower alkylthio lower alkyl
lower alkoxyalkyl
hydroxyhalo lower alkyl
lower alkoxy-substituted phenyl
monocyclic heterocyclic-substituted lower alkyl
lower alkyl substituted phenylthio
lower alkyl sulphonyl
phenyl lower alkylthio
lower alkyl substituted phenyl lower alkyl
hydroxy lower alkyl
phenyl lower alkyl The various lower alkyl, lower alkoxy and lower alkylthio moieties may contain from 1 to 6 carbon atoms.

In this specification there are set out a very considerable number of specific pyrimidine derivatives and methods for their preparation. It is a matter of simple chemistry and of comparative ease for the skilled man in the art to prepare a particular pyrimidine derivative differing from any derivatives not specifically mentioned in this specification merely in the number of carbon atoms in any lower alkyl, lower alkenyl, or lower alkoxy moiety, or substituent incorporating such as moiety. All that it is necessary to do is to commence with the appropriate reactants, and, if necessary, adjust the reaction conditions. It is not a practicable reality to recite, by name, each and every simple variation possible.

The heterocyclic rings for $R_2$, or for $R_1$ together with their adjacent N-atom, or for $R_4$ may contain any number of ring atoms. Preferred rings, however, contain 5- or 6- ring atoms, and of the ring atoms one or more of these may be constituted by additional hetero-atoms. The heterocyclic rings may also bear simple substituents. Thus, they may be, for example, morpholine, pyridyl, pyrrole, piperazine, piperidine or tetrazole rings, but other rings such as, for example, aziridine, azepine, triazine, thiazole, imidazole, piprazole indole, indazole, purine, benzimidazole, pyrollidine, isoxazole, phenothiazine, and the like are considered within the scope of the invention. $R_3$ and $R_4$ may be halogen atoms, for example chlorine, bromine, fluorine or iodine. Halogen-containing substituents may likewise contain any of these four.

$R_3$ and $R_4$ may constitute an alkylene or alkenylene bridge, and this may contain 2 or more carbon atoms; thus it may be, for example, a trimethylene bridge.

A surface active agent may or may not be present in the fungicidal compositions of the invention, but it is preferred that one should be present, more especially if the composition is one based upon a liquid diluent.

In a further aspect, therefore, the invention provides a fungicidal composition comprising, as an active ingredient, a fungicidally effective amount of a pyrimidine derivative of the general formula:

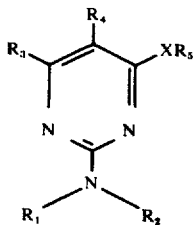

or a fungicidally effective amount of a salt thereof, wherein $R_1$ stands for hydrogen, lower alkyl, lower alkenyl, or phenyl-lower alkyl; $R_2$ is hydrogen, lower alkyl, lower alkenyl, lower alkyl-phenyl, halo-phenyl, lower alkoxy-carbonyl phenyl, amino, anilino, cyano, lower alkylcarbonyl, halo-lower alkylcarbonyl, a nitrogen-containing monocyclic heterocyclic radical, phenyl-lower alkyl, lower alkyl substituted by a 6-membered heterocyclic nitrogen-containing radical, cycloalkyl, carbamoyl, or nitro-substituted phenylsulphonyl; or $R_1$ and $R_2$, together with the adjacent nitrogen atom, form 5- or 6- membered a heterocyclic ring which may contain one or more additional heterocyclic atoms, or form a guanidino or benzylidine-hydrazino group; $R_3$ is hydrogen, halogen, lower alkyl, lower alkylthio-lower alkyl, or unsubstituted or halo- or lower alkoxy-substituted phenyl; $R_4$ is hydrogen, halogen, lower alkyl, phenyl- lower alkyl, lower alkenyl, lower alkoxyalkyl, hydroxyhalo- lower alkyl nitro, phenylazo, monocyclic heterocyclic substituted lower alkyl, phenyl, phenyloxy, halo substituted phenylthio, lower alkyl-substituted phenylthio, lower alkyl-sulphonyl, phenyl-lower alkylthio, lower alkyl-substituted phenyl lower alkyl, halo-substituted phenyl-lower alkyl, or a —CHO group; or $R_3$ and $R_4$ together form a lower alkylene or lower alkenylene bridging group; X is an atom of oxygen or sulphur; $R_5$ is hydrogen, hydroxy-lower alkyl, phenyl-lower alkyl, lower alkenyl, lower alkoxycarbonyl-lower alkyl, lower alkyl-carbonyl-lower alkyl, di-lower alkylamino-lower alkyl, lower alkylthio-lower alkyl, lower alkoxy-lower alkyl, or phenylcarbonylox lower alkyl, and a carrier for the active ingredient comprising an inert solid diluent, or a liquid diluent containing a surface active agent.

In a more detailed aspect the invention provides a fungicidal composition comprising, as an active ingredient, a fungicidally effective amount of a pyrimidine derivative of the general formula:

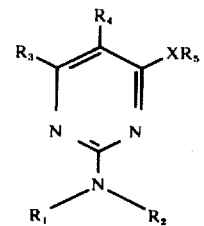

or a fungicidally effective amount of a salt thereof, wherein $R_1$ stands for hydrogen, allyl, methyl, ethyl, propyl and butyl or benzyl; $R_2$ is hydrogen, methyl, ethyl, propyl, butyl, allyl, chloro, phenyl, bromo-phenyl, ethoxy, carboxyphenyl, amino, anilino, cyano, methylcarbonyl, trifluoromethyl carbonyl, chloromethyl carbonyl, benzyl, 3(4-morpholino) propyl, 2-pyridyl, cyclohexyl, carbamoyl, or nitro-phenyl sulphonyl; or $R_1$ and $R_2$ together with the adjacent nitrogen atom form guanidino, benzylidinehydrazino, pyrrole, morpholine, 4-methylpiperazine, piperidine, or tetrazole; $R_3$ is hydrogen, chloro, methyl, ethyl, propyl, hexyl, ethylthio-methyl, phenyl, chloro-phenyl or methoxy phenyl; $R_4$ is hydrogen, bromo, lower alkyl, benzyl, allyl, butenyl, ethoxy ethyl, trichlorohydroxyethyl, nitro, phenylazo, piperid-1-yl methyl, phenyl, phenyloxy, chloro phenylthio, methyl phenylthio, methyl sulphonyl, benzylthio, dimethyl benzyl, chlorobenzyl, dichlorobenzyl or —CHO; or $R_3$ and $R_4$ together form a trimethylene bridging group; X is an atom of oxygen or sulphur; $R_5$ is hydrogen, hydroxy ethyl, methoxymethyl, benzyl, allyl, methyl carboxyethyl, methyl carbonyl methyl, di-ethyl-amino-ethyl, dimethyl amino ethyl, ethyl thio ethyl, phenyl carbonyloxy methyl, or ethoxy ethyl, and a carrier for the active ingredients selected from the group consisting of an inert solid, and a liquid diluent containing a surface active agent.

In another, preferred aspect, the invention provides a fungicidal composition wherein the active ingredient is one of the indicated formula wherein $R_1$ is hydrogen, lower alkyl, lower alkenyl, or phenyl-lower alkyl; $R_2$ is hydrogen, lower alkyl, lower alkenyl, unsubstituted or halo-, lower alkyl-, or lower alkoxycarbonyl-substituted phenyl, amino, anilino, cyano, lower alkylcarbonyl, phenyl-lower alkyl, heterocyclic-lower alkyl or carbamoyl; or $R_1$ and $R_2$ together with the adjacent nitrogen form a 5- or 6- membered heterocyclic ring; $R_3$ is H, lower alkyl, phenyl, or lower alkylthio-lower alkyl; $R_4$ is hydrogen, halogen, lower alkyl, phenyl-lower alkyl, lower alkenyl, lower alkoxy-lower alkyl, hydroxyhalo-lower alkyl, lower alkyl group substituted by a nitrogen-containing monocyclic heterocyclic radical, or lower alkylsulphonyl; X is oxygen or sulphur; $R_5$ is hydrogen, hydroxy-lower alkyl, lower alkylcarbonyl-lower alkyl, di-lower alkylamino-lower alkyl, or lower alkylthio-lower alkyl; and a carrier for the active ingredient comprising a solid diluent or a liquid diluent containing a surface active agent.

In a further, particularly preferred aspect, the invention provides a fungicidal composition wherein the active ingredient is one of the indicated formula wherein $R_1$ and $R_2$ are hydrogen or lower alkyl, or $R_1$ and $R_2$ together with the adjacent nitrogen atom form a 5- or 6- membered heterocyclic ring; $R_3$ is lower alkyl; $R_4$ is lower alkyl or lower alkenyl; $R_5$ is hydrogen; and X is an atom of oxygen or sulphur; and a carrier for the active ingredient comprising an inert solid diluent, or an inert liquid diluent containing a surface active agent.

In a yet a further, and especially preferred aspect, the invention provides a fungicidal composition wherein the active ingredient is one of the indicated formula, or a salt thereof, wherein $R_1$ and $R_2$ are hydrogen or lower alkyl or lower alkenyl or $R_1$ and $R_2$ together with the adjacent nitrogen atom form a heterocyclic ring; $R_3$ is lower alkyl; $R_4$ is lower alkyl or lower alkenyl; $R_5$ is hydrogen; and X is an atom of oxygen or sulphur; and a carrier for the active ingredient comprising a solid diluent, or a liquid diluent containing a surface active agent.

A particularly useful fungicidal composition and one having especially potent and useful properties, is one of the indicated formula wherein the active ingredient is a compound, or a salt thereof, in which $R_1$ is hydrogen, allyl, ethyl, propyl or butyl and $R_2$ is selected from allyl, methyl, ethyl, propyl and butyl, $R_3$ is selected from methyl and ethyl, $R_4$ is selected from methyl, ethyl, propyl, butyl, and amyl, $R_5$ is hydrogen and X is oxygen; and an adjuvant therefor.

The pyrimidine derivatives are, for convenience, referred to throughout the present specification and claims as having the formula:-

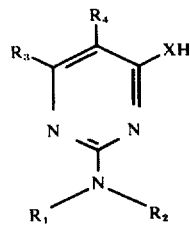

where X is sulphur or oxygen. The compounds, however, also exist with tautomeric structures of the following form:

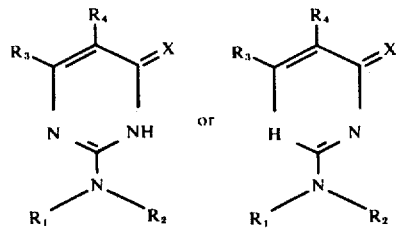

and the present invention is to be understood as including the tautomeric forms of such compounds.

Specific pyrimidine derivatives of the invention which have been found to be particularly useful as listed in Tables I to III below. In Table I are listed hydroxypyrimidines and in Tables II and III there are set out various O- and S- etherified pyrimidine derivatives. In Table IV there are set out various salts of hydroxypyrimidine. The groups $NR_1R_2$, $R_3$ and $R_4$ in Table I, and additionally the groups $XR_5$ in Tables II and III correspond to Formulas I and II below.

In all three of these Tables melting points (m.p.) and boiling points (b.p.) are expressed in degrees Centigrade.

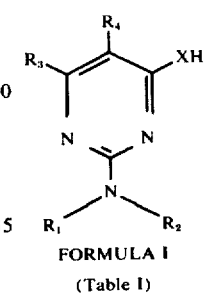 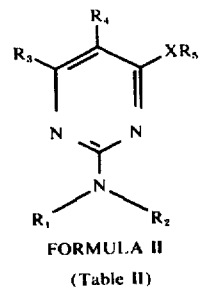

FORMULA I      FORMULA II
(Table I)      (Table II)

In this specification the numbering of the pyrimidine ring is as follows:

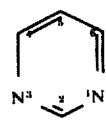

It may be noted that the 4- and 6- positions are equivalent.

TABLE I

| | HYDROXYPYRIMIDINES (wherein X of Formula I is O) the compounds marked * are new compounds. | | | |
|---|---|---|---|---|
| COMPOUND NO: | $NR_1R_2$ | $R_3$ | $R_4$ | PHYSICAL CHARACTERISTICS |
| * 1 | —NH . CN | $CH_3$ | $nC_4H_9$ | m.p. 295–298° |
| * 2 | —N($CH_3$)$_2$ | $CH_3$ | $nC_5H_{11}$ | m.p. 84° |
| * 3 | —N($CH_3$)$_2$ | $CH_3$ | $nC_3H_7$ | m.p. 120° |
| 4 | —N($CH_3$)$_2$ | $CH_3$ | $nC_4H_9$ | m.p. 102° |
| * 5 | —N($CH_3$)$_2$ | $CH_3$ | $nC_6H_{13}$ | m.p. 80° |
| 6 | —$NH_2$ | $CH_3$ | $nC_4H_9$ | m.p. 257° |
| 7 | —N($CH_3$)$_2$ | $CH_3$ | Br | m.p. 232–233° |
| 8 | —$NH_2$ | $CH_3$ | —$CH_2$—C$_6$H$_5$ | m.p. 277.5–278.5° |
| * 9 | —N⟨pyrrolidinyl⟩ | $CH_3$ | $nC_4H_9$ | m.p. 149° |

TABLE I-continued

HYDROXYPYRIMIDINES (wherein X of Formula I is O)
the compounds marked * are new compounds.

| COMPOUND NO: | NR₁R₂ | R₃ | R₄ | PHYSICAL CHARACTERISTICS |
|---|---|---|---|---|
| *10 | -N(morpholino) | CH₃ | nC₄H₉ | m.p. 192–195° |
| *11 | -N(CH₃)₂ | C₂H₅ | H | m.p. 140° |
| 12 | -N(CH₃)₂ | CH₃ | -CH₂-CH=CH₂ | m.p. 174° |
| *13 | -NH-C₆H₄.Br(p) | CH₃ | nC₄H₉ | m.p. 176° |
| *14 | -NH-C₆H₄-CO.OC₂H₅(p) | CH₃ | nC₄H₉ | m.p. 147–150° |
| *15 | -NH-C₆H₄-CH₃ (p) | CH₃ | nC₄H₉ | m.p. 185–187° |
| *16 | -N(4-methylpiperazino) | CH₃ | nC₄H₉ | m.p. 162–164° |
| *17 | -N(CH₃)₂ | CH₃ | -CH₂-C₆H₅ | m.p. 188–190° |
| *18 | -N(CH₃)₂ | C₆H₅ | nC₄H₉ | m.p. 182° |
| *19 | -N(CH₃)₂ | CH₃ | -CH(CH₃)₂ | m.p. 181–183° |
| *20 | -NH-(CH₂)₃-N(morpholino) | CH₃ | nC₄H₉ | m.p. 139–141° |
| *21 | -N[CH₂-C₆H₅]₂ | CH₃ | nC₄H₉ | m.p. 151° |
| *22 | -NH-CO-NH₂ | CH₃ | nC₄H₉ | m.p. 207° |
| *23 | -NH-NH-C₆H₅ | CH₃ | nC₄H₉ | m.p. 185° |
| *24 | -N(piperidino) | CH₃ | -CH₂-N(piperidino) | m.p. 212–216° |
| *25 | -N(nC₄H₉)₂ | CH₃ | nC₄H₉ | m.p. 145–148° |
| 26 | -NH-NH₂ | CH₃ | nC₄H₉ | m.p. 201–212° |
| *27 | -NH-CO-CH₃ | CH₃ | nC₄H₉ | m.p. 153° |
| *28 | -NH-CH(CH₃)₂ | CH₃ | nC₄H₉ | m.p. 135–137° |
| *29 | -NH-CH₂-C₆H₅ | CH₃ | nC₄H₉ | m.p. 76° |
| *30 | NHC₂H₅ | CH₃ | nC₄H₉ | m.p. 159° |
| *31 | -N(CH₃)₂ | CH₃-CH₂-SCH₂ | H | m.p. 118° |
| *32 | -N(CH₃)₂ | CH₃ | CH₃CH₂.OCH₂CH₂— | m.p. 104–105° |
| *33 | -N(CH₃)₂ | H | nC₄H₉ | m.p. 84° |
| *34 | -NHnC₄H₉ | CH₃ | nC₄H₉ | m.p. 143° |
| *35 | -N(CH₃)₂ | CH₃ | CH₃-SO₂— | m.p. 235° |
| 37 | -NH₂ | CH₃ | CH₂CH=CH₂ | m.p. 266–267° |
| 38 | -N(CH₃)₂ | CH₃ | CH(OH)CCl₃ | m.p. 221–222° (with decomposition) |
| 39 | -N(CH₃)₂ | H | CH(OH)CCl₃ | m.p. 228–229° (with decomposition) |
| *40 | -NH-CH₃ | CH₃ | CH(OH)CCl₃ | m.p. 196° |
| 41 | -NH-(2-pyridyl) | CH₃ | H | m.p. 205–207° |
| *42 | -NH-CH₂.CH=CH₂ | CH₃ | nC₄H₉ | m.p. 165–167° |
| 43 | N(CH₃)₂ | H | NO₂ | m.p. 301° |
| *44 | -N(morpholino) | CH₃ | CH₃ | m.p. 201° |

TABLE I-continued

HYDROXYPYRIMIDINES (wherein X of Formula I is O)
the compounds marked * are new compounds.

| COMPOUND NO: | $NR_1R_2$ | $R_3$ | $R_4$ | PHYSICAL CHARACTERISTICS |
|---|---|---|---|---|
| * 45 | −N(CH₂CH₂)₂O (morpholino) | $nC_3H_7$ | H | m.p. 174–175° |
| * 46 | −N(CH₂)₅ (piperidino) | $CH_3$ | $CH_3$ | m.p. 157° |
| * 47 | $-N(CH_3)_2$ | $CH_3$ | $C_2H_5$ | m.p. 141° |
| 48 | $-N(CH_3)_2$ | H | H | m.p. 175–176° |
| 49 | $-NH_2$ | $CH_3$ | $nC_5H_{11}$ | m.p. 234° |
| 50 | $-NH_2$ | $CH_3$ | $nC_6H_{13}$ | m.p. 236° |
| 51 | $-NH_2$ | $CH_3$ | $CH_3$ | m.p. 304–306° |
| * 52 | $N(CH_3)_2$ | $nC_3H_7$ | H | m.p. 127° |
| * 53 | −N(CH₂CH₂)₂O (morpholino) | $CH_3$ | $nC_3H_7$ | m.p. 238° |
| * 54 | −N(CH₂)₅ (piperidino) | $CH_3$ | $nC_4H_9$ | m.p. 126° |
| * 55 | $N(CH_3)_2$ | phenyl | H | m.p. 243° |
| * 56 | $N(CH_3)_2$ | —(CH₂)₃— (fused ring) | | m.p. 224–225° |
| 57 | $N(CH_3)_2$ | $CH_3$ | −N=N−C₆H₅ | m.p. 147–150° |
| * 58 | $N(CH_3)_2$ | $CH_3$ | $nC_8H_{17}$ | m.p. 57° |
| * 59 | $N(CH_3)_2$ | $CH_3$ | $-CH_2.N(CH_3)_2 \cdot HCl$ | m.p. 280–290° |
| * 60 | $N(CH_3)_2$ | $nC_6H_{13}$ | H | m.p. 80–81° |
| 61 | $NH.NH_2$ | $CH_3$ | $nC_3H_7$ | m.p. 216–218° |
| * 62 | $NH.C_3H_7n$ | $CH_3$ | $nC_4H_9$ | m.p. 154° |
| * 63 | $N(CH_3)_2$ | $CH_3$ | iso $C_4H_9$ | m.p. 150° |
| * 64 | $N(CH_3)_2$ | H | $CH_2=CH-CH_2$ | m.p. 94° |
| * 65 | $N(CH_3)_2$ | $CH_3$ | $(CH_3)_2.CH.CH_2.CH_2$ | m.p. 151° |
| * 66 | $NH.CO.CF_3$ | $CH_3$ | $nC_4H_9$ | m.p. 128–129° |
| * 67 | $N(CH_3)_2$ | $nC_3H_7$ | $C_2H_5$ | m.p. 103–104° |
| * 68 | $N(CH_3)_2$ | $CH_3$ | 4-Cl-C₆H₄-S- | m.p. 210° |
| * 69 | $NH.COCH_2Cl$ | $CH_3$ | $nC_4H_9$ | m.p. 156° |
| * 70 | $N(CH_3)_2$ | $C_2H_5$ | $nC_4H_9$ | m.p. 100° |
| * 71 | $N(CH_3)_2$ | $CH_3$ | 4-CH₃-C₆H₄-S- | m.p. 220° |
| * 72 | $N(CH_3)_2$ | $CH_3$ | C₆H₅-CH₂-S- | m.p. 175–176° |
| * 73 | $NH_2.C(=NH)-NH-$ | $CH_3$ | $nC_3H_7$ | m.p. 291–293° |
| 74 | C₆H₅-CH=N-NH- | $CH_3$ | $nC_3H_7$ | m.p. 199° |
| * 75 | $-N(CH_3)(C_2H_5)$ | $CH_3$ | $nC_4H_9$ | m.p. 101° |
| * 76 | $-N(CH_3)(C_2H_5)$ | $CH_3$ | $nC_3H_7$ | m.p. 116–117° |
| * 77 | $-N(C_2H_5)_2$ | $CH_3$ | $nC_3H_7$ | m.p. 114–115° |

TABLE I-continued

HYDROXYPYRIMIDINES (wherein X of Formula I is O)
the compounds marked * are new compounds.

| COMPOUND NO: | $NR_1R_2$ | $R_3$ | $R_4$ | PHYSICAL CHARACTERISTICS |
|---|---|---|---|---|
| * 78 | $-NH \cdot SO_2-\text{C}_6\text{H}_4-NO_2$ | $CH_3$ | $CH_2=CH-CH_2-$ | m.p. 233–234° |
| * 79 | $NH \cdot CO \cdot CH_3$ | H | phenoxy ($C_6H_5-O-$) | m.p. 230–231° |
| 80 | $NH_2$ | H | benzyl ($C_6H_5-CH_2-$) | m.p. 268–270° |
| * 81 | $NH \cdot CO \cdot CH_3$ | H | benzyl | m.p. 307° |
| * 82 | $N(CH_3)_2$ | $CH_3$ | 2,4,6-trimethylbenzyl | m.p. 182° |
| * 83 | $N(CH_3)_2$ | $CH_3$ | 4-chlorobenzyl ($Cl-C_6H_4-CH_2-$) | m.p. 220° |
| * 84 | cyclohexyl-NH- | $CH_3$ | $nC_3H_7$ | m.p. 220° |
| 85 | $N(CH_3)_2$ | $CH_3$ | 2,3-dichlorobenzyl ($-CH_2-C_6H_3Cl_2$) | m.p. 140° |
| * 86 | morpholino ($-N(CH_2CH_2)_2O$) | H | $CH(OH)CCl_3$ | m.p. 202–203° |
| * 87 | 4-methylpiperazino ($-N(CH_2CH_2)_2N-CH_3$) | H | $CH(OH)CCl_3$ | m.p. 205° |
| * 88 | pyrrolidino ($-N(CH_2)_4$) | $CH_3$ | $CH(OH)CCl_3$ | m.p. 213° |
| * 89 | $-NHC_2H_5$ | H | $CH(OH)CCl_3$ | m.p. 188–190° |
| * 90 | $N(C_2H_5)_2$ | $CH_3$ | $C_2H_5$ | m.p. 121–122° |
| * 91 | $N(C_2H_5)_2$ | $CH_3$ | $-CH_2-CH=CH_2$ | m.p. 110–111° |
| * 92 | $N(CH_3)_2$ | H | $C_2H_5$ | m.p. 124–125° |
| * 93 | $N(CH_3)_2$ | phenyl | $CH_2=CH \cdot CH_2-$ | m.p. 196° |
| * 94 | $N(CH_3)_2$ | 4-chlorophenyl | H | m.p. 260–261° |
| * 95 | $N(CH_3)_2$ | phenyl | $C_2H_5$ | m.p. 175° |
| * 96 | $NH-\text{C}_6\text{H}_4-CO \cdot OC_2H_5$ | $CH_3$ | $nC_3H_7$ | m.p. 217–219° |

TABLE I-continued

HYDROXYPYRIMIDINES (wherein X of Formula 1 is O)
the compounds marked * are new compounds.

| COMPOUND NO: | $NR_1R_2$ | $R_3$ | $R_4$ | PHYSICAL CHARACTERISTICS |
|---|---|---|---|---|
| * 97 | NH—C₆H₄—Cl (4-chlorophenylamino) | $CH_3$ | $nC_3H_7$ | m.p. 216–218° |
| * 98 | $N(CH_3)_2$ | $CH_3$ | 4-methoxyphenyl (—O—C₆H₄—) | m.p. 280–281° |
| * 99 | $NHC_2H_5$ | $CH_3$ | 4-methoxyphenyl | m.p. 199° |
| 100 | $NH_2$ | $CH_3$ | $C_2H_5$ | m.p. 288–289° |
| 101 | $NH_2$ | Cl | H | m.p. 261° |
| 102 | $NH_2$ | $CH_3$ | Br | m.p. 267–269° |
| * 103 | —NH—C₆H₄—Cl with guanidino (NH—C(=NH)—NH—C₆H₄—Cl) | $CH_3$ | $CH_3$ | m.p. 268–270° |
| 104 | $NH.CH.(CH_3)_2$ | naphthyl (fused ring system) | | m.p. 212–213° |
| 105 | $N(CH_3)_2$ | $CH_3$ | H | m.p. 175–176° |
| * 106 | $N(CH_3)_2$ | $N(CH_3)_2$ (fused ring with N=...—OH) | | m.p. above 340° |
| 107 | piperidino (—N⟨CH₂⟩₅) | $CH_3$ | CHO | m.p. 235° |
| * 108 | 1,2,4-triazol-1-yl (—N—N=N—N) | $CH_3$ | H | m.p. 220–222° |
| * 109 | $—NHC_2H_5$ | $CH_3$ | $—CH_2$—C₆H₅ | m.p. 174° |
| * 110 | $—NHC_2H_5$ | $CH_3$ | $nC_5H_{11}$ | m.p. 148–149° |
| * 111 | $—NHC_2H_5$ | $CH_3$ | $—CH_2.CH_2.CH(CH_3)_2$ | m.p. 182° |
| * 112 | $—NHC_2H_5$ | $CH_3$ | $—CH_2CH=CH_2$ | m.p. 147° |
| * 113 | $—NHC_2H_5$ | $CH_3$ | $n—C_3H_7$ | m.p. 166° |
| * 114 | $—NHC_2H_5$ | $CH_3$ | $—CH_2.CH(CH_3)_2$ | m.p. 198° |
| * 115 | $—NHC_2H_5$ | $CH_3$ | $—CH_2.CH=CHCH_3$ | m.p. 150.5–151° |
| * 116 | $—NHC_2H_5$ | H | $n.C_4H_9$ | m.p. 163–164° |
| * 117 | $—N(C_2H_5)_2$ | $CH_3$ | $n.C_4H_9$ | m.p. 109.5–110° |
| * 118 | $—N(CH_3)_2$ | $CH_3$ | $—CH_2.CH=CHCH_3$ | m.p. 137° |
| * 119 | $N(CH_2—CH=CH_2)_2$ | $CH_3$ | $n.C_4H_9$ | m.p. 104–105° |

In the above table the compounds numbered 42, 91, 92, 93, 103 and 106 were prepared by the procedure described in Example 1 below, using the appropriate reactants. The compounds numbered 40, 86, 87, 88 and 89 were prepared by a method analogous to that described in the literature by Hull, JCS 1957, 4845.

TABLE II

ETHERIFIED HYDROXYPYRIMIDINES of general Formula II
(wherein X = O)
All these compounds are new compounds.

| COMPOUND NO: | $NR_1R_2$ | $R_3$ | $R_4$ | $XR_5$ | PHYSICAL CHARACTERISTICS |
|---|---|---|---|---|---|
| *120 | —$N(CH_3)_2$ | $CH_3$ | $nC_4H_9$ | O—$CH_2$—$CH_2$—OH | b.p. 126–128°/0.4 mm |
| *121 | —$N(CH_3)_2$ | $CH_3$ | $nC_4H_9$ | O . $CH_2$—$CH_2$—$N(C_2H_5)_2$ | b.p. 126–128°/0.23 mm |
| *122 | $N(CH_3)_2$ | H | H | O . $CH_2$—C$_6$H$_5$ | b.p. 118–120°/0.1 mm |
| *123 | $N(CH_3)_2$ | H | H | O . $CH_2$ . CH=$CH_2$ | b.p. 60–65°/0.1 mm |
| *124 | $N(CH_3)_2$ | $CH_3$ | $CH_3$ | O . $CH_2$ . $CH_2OH$ | m.p. 79–80° |
| 125 | $N(CH_3)_2$ | $CH_3$ | $nC_4H_9$ | $OCH_2OCO$—C$_6$H$_5$ | $n_D^{24}$ 1.5417 |
| 126 | $N(CH_3)_2$ | $CH_3$ | $nC_4H_9$ | $OCH_2$ . $OCH_3$ | b.p. 96–100°/0.03 mm |

TABLE III

SULPHUR-CONTAINING PYRIMIDINES of General Formula II
(wherein X = S)

| COMPOUND NO: | $NR_1R_2$ | $R_3$ | $R_4$ | $XR_5$ | PHYSICAL CHARACTERISTICS |
|---|---|---|---|---|---|
| *127 | —$N(CH_3)_2$ | $CH_3$ | $nC_4H_9$ | —SH | m.p. 105–106° |
| *128 | —$N(CH_3)_2$ | $CH_3$ | $nC_4H_9$ | —S—$CH_2$—C(=O)—$CH_3$ | m.p. 48° |
| *129 | —$N(CH_3)_2$ | $CH_3$ | $C_2H_5$ | SH | m.p. 140–141° |
| *130 | —$N(CH_3)_2$ | $CH_3$ | $nC_4H_9$ | —S—$CH_2$—$CH_2$—$N(CH_3)_2$ | b.p. 153°/0.23 mm $n_D^{23}$ 1.5452 |
| *131 | —$N(CH_3)_2$ | $CH_3$ | $nC_4H_9$ | —S—$CH_2$—$CH_2S$—$C_2H_5$ | b.p. 160°/0.33 mm $n_D^{25}$ 1.5670 |
| *132 | $N(CH_3)_2$ | $CH_3$ | $nC_4H_9$ | —S . $CH_2$—C$_6$H$_5$ | m.p. 52–53° |
| *133 | $N(CH_3)_2$ | $CH_3$ | $nC_4H_9$ | —S . S—pyrimidinyl($nC_4H_9$, $N(CH_3)_2$) | m.p. 60–62° |
| *134 | $N(CH_3)_2$ | $CH_3$ | $CH_3$ | SH | m.p. 162–163° |
| *135 | $N(CH_3)_2$ | $CH_3$ | $nC_4H_9$ | S . $CH_2CH_2OC_2H_5$ | b.p. 146°/0.5 mm |
| *136 | $N(CH_3)_2$ | $CH_3$ | H | SH | m.p. 154–155° |
| 137 | $N(CH_3)_2$ | H | H | SH | m.p. 149° |
| *138 | $N(CH_3)_2$ | $CH_3$ | $nC_4H_9$ | S . $CH_2$ . CO . $C_2H_5$ | m.p. 64° |
| *139 | $N(CH_3)_2$ | $CH_3$ | $nC_4H_9$ | S . $CH_2$ . $CH_2$ . $N(C_2H_5)_2$ | b.p. 150°/0.22 mm $n_D^{23}$ 1.5411 |

The active ingredients of the fungicidal compositions of the invention are amphoteric and the invention accordingly includes, as stated above, fungicidal compositions wherein the active ingredient is in the form of a salt of any of the pyrimidine derivatives defined above. Accordingly references in this specification to "pyrimidine derivatives" are to be construed as including salts of the pyrimidine derivatives.

The salts of the pyrimidine derivatives may be metal, or acid salts. Suitable metal salts include alkali metal salts, for example the sodium and potassium salts, or salts of noble metals, for example, silver salts. Other suitable metal salts include the di-mercury and mercuri-chloride salts. Suitable acid salts include salts formed from organic or inorganic acids. Organic acids which may be used include:

para-toluenesulphonic acid.
2,4,6-trinitrobenzenesulphonic acid,
3,5-dinitrobenzoic acid,
oxalic acid,
trichloroacetic acid,
citric acid,
picric acid.

Inorganic acids which may be used include:
hydrochloric acid,
hydrobromic acid,
nitric acid,
sulphuric acid,
phosphoric acid,
fluoroboric acid,
thiocyanic acid,
perchloric acid.

A preferred salt is an alkali metal salt or a hydrohalide, especially the latter. A salt which is a hydrochloride of a pyrimidine d derivative is particularly preferred.

Specific examples of salts according to the invention are set out in Table IV below.

TABLE IV

| COMPOUND NO: | EXAMPLE NO: | PARENT COMPOUND NO. (TABLE I) | SALT | PHYSICAL CHARACTERISTIC |
|---|---|---|---|---|
| 140 | 16 | 4 | Hydrochloride | 167° C |
| 141 | 20 | 4 | Potassium | 310–316° C (D) |
| 142 | 21 | 4 | Sodium | 285° C |
| 143 | 22 | 4 | p-toluene sulphonate | 148° C |
| 144 | 23 | 4 | fluoroborate | 122–123° C |
| 145 | 24 | 4 | hydrobromide | |
| 146 | 25 | 4 | thiocyanate | 129–130° C |
| 147 | 26 | 4 | dipyrimidinyl mercury | 202–205° C |
| 148 | 27 | 4 | Silver | 190–194° |
| 149 | 28 | 4 | mercurichloride | 250–255° C |
| 150 | 29 | 4 | oxalate | 132° C |
| 151 | 30 | 4 | 2,4,6 trinitrobenzene sulphonate | 209–210° C |
| 152 | 31 | 4 | 3,5-dinitrobenzoate | 159° C |
| 153 | 32 | 4 | trichloroacetate | 95° C |
| 154 | 33 | 4 | picrate | 182–183° C |
| 155 | 34 | 30 | acid oxalate | 182° C |
| 156 | 35 | 30 | oxalate | 162–164° C |

HYDROXY PYRIMIDINE SALTS

| COMPOUND NO: | EXAMPLE NO: | PARENT COMPOUND NO. (TABLE I) | SALT | PHYSICAL CHARACTERISTIC |
|---|---|---|---|---|
| 157 | 36 | 30 | p-toluene sulphonate | 187° C |
| 158 | 37 | 30 | 2,4,6-trinitrobenzene sulphonate | 215–218° C |
| 159 | 38 | 30 | trichloroacetate | 118° C (D) |
| 160 | 39 | 30 | citrate | 154° C |
| 161 | 40 | 30 | picrate | 247–249° C |
| 162 | 41 | 30 | hydrochloride | 173–174° C |
| 163 | 42 | 30 | hydrobromide | 201–202° C |
| 164 | 43 | 30 | perchlorate | 96–97° C |
| 165 | 44 | 30 | thiocyanate | 186–188° C |
| 166 | 45 | 30 | mercurichloride | 201° C |
| 167 | 46 | 30 | dipyrimidinyl mercury | 232–234° C |
| 168 | 47 | 30 | Silver | 250–225° C |

A particularly useful pyrimidine derivative is that in which $R_1$ and $R_2$ are both methyl, $R_3$ is methyl, $R_4$ is $nC_4H_9$, and $XR_5$ is OH, that is compound No. 4 in the foregoing Table I, (page 12). Other particularly useful pyrimidine derivatives are those having the following compound numbers in the foregoing Tables: 2, 3, 9, 12, 28, 30, 37, 62, 70, 75, 91, 117, 129, 130 and 139, especially compound No. 30. According to a preferred embodiment of the invention, therefore, we provide fungicidal compositions comprising as active ingredient, 2-dimethylamino-4-methyl-5-n-butyl-6-hydroxypyrimidine or 2-ethylamino-4-methyl-5-n-butyl-6-hydroxypyrimidine; or a salt thereof; and a carrier therefor comprising a solid diluent, or a liquid diluent containing a surface active agent.

In a further aspect the invention provides fungicidal composition containing as an active ingredient a compound selected from:

2-dimethylamino-4-methyl-5-n-pentyl-6-hydroxypyrimidine,
2-dimethylamino-4-methyl-5-n-propyl-6-hydroxypyrimidine,
2-N-pyrrolidino-4-methyl-5-n-butyl-6-hydroxypyrimidine,
2-dimethylamino-4-methyl-5-allyl-6-hydroxypyrimidine,
2-isopropylamino-4-methyl-5-n-butyl-6-hydroxypyrimidine,
2-amino-4-methyl-5-allyl-6-hydroxypyrimidine,
2-n-propylamino-4-methyl-5-n-butyl-6-hydroxypyrimidine,
2-dimethylamino-4-ethyl-5-n-butyl-6-hydroxypyrimidine,
2-ethylmethylamino-4-methyl-5-n-butyl-6-hydroxypyrimidine,
2-diethylamino-4-methyl-5-allyl-6-hydroxypyrimidine,
2-diethylamino-4-methyl-5-n-butyl-6-hydroxypyrimidine,
2-dimethylamino-4-methyl-5-ethyl-6-mercaptopyrimidine,
2-dimethylamino-4-methyl-5-n-butyl-6(2-dimethylaminoethylthio-) pyrimidine,
2-dimethylamino-4-methyl-5-n-butyl-6-(2-diethylaminoethylthio-) pyrimidine;

or a salt thereof; and a carrier for the active ingredient selected from the group comprising an inert solid, and a liquid diluent containing a wetting agent.

The fungicidal compositions of the invention possess activity against a wide variety of fungal diseases including the specific diseases recited below, particularly those makred with an asterisk.

| | |
|---|---|
| *Puccinia recondita* | (brown rust) on wheat |
| *Phytophthora infestans* | (late blight) on tomatoes |
| * *Sphaerotheca fuliginea* | (powdery mildew) on cucumber |
| * *Erysiphe graminis* | (powdery mildew) on wheat and barley |
| *Podosphaera leucotricha* | (powdery mildew) on apple |
| *Uncinula necator* | (powdery mildew) on vine |
| *Plasmopara viticola* | (downy mildew) on vine |
| *Piricularia oryzae* | (blast) on rice |
| *Venturia inaequalis* | (scab) on apple |
| *Pythium ultimum* | on peas |
| *Fusarium culmoram* | on wheat |

A particularly useful feature of the activity of the pyrimidine derivatives listed above is their systemic effect, that is to say, their ability to move in a planet to combat an infection or infestation thereof remote from a site of initial application of a compound. Thus a compound of the invention or a composition containing the same may be applied to the soil surrounding the roots of a plant and be taken up by the plant through its roots to combat pests such as fungi on the plants.

The fungicidal compositions of the invention can be used to prevent injury due to fungi in a number of ways. Thus they can be applied to the locus to be protected, for example to the foliage or roots of a plant or to seed, or to the soil in which plants are growing or to be planted.

In a further aspect the invention includes a method for the combating of undesired fungal infections in growing plants which comprises applying to the locus of the plants a pyrimidine derivative as hereinbefore defined.

In yet a further aspect the invention includes a method for treating agricultural soil comprising applying to the soil a pyrimidine derivative as hereinbefore defined.

The invention includes, therefore, a method of combating plant fungal pathogens in which a plant susceptible to such pathogens, or seed thereof, is contacted with a pyrimidine derivative as hereinbefore defined. Either the foliage, or the roots (e.g. through the soil) of plants may be contacted with the pyrimidine derivative.

The compositions may be used for agricultural and horticultural purposes and the type of composition used in any instance will depend upon the particular purpose for which it is to be used.

The compositions may be in the form of dusting powders or granules wherein the active ingredient is mixed with a solid diluent or carrier. Suitable solid diluents or carriers may be, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent assisting the adhesion of the composition to the seed, for example a mineral oil.

The compositions may also be in the form of dispersible powders or grains comprising, in addition to the active ingredient, a wetting agent to facilitate the dispersion of the powder or grains in liquids. Such powders or grains may include fillers, suspending agents and the like.

The compositions may also be, and preferably are, in the form of liquid preparations to be used as soil drenches, sprays or dips which are generally aqueous solutions, dispersions, or emulsions containing the active ingredient, if desired in the presence of one or more wetting agents, dispersing agents, emulsifying agents, suspending agents or corrosion inhibitors (e.g. lauryl isoquinolinium bromide). Water or organic liquids may be used to prepared solutions, dispersions or emulsions of the active ingredient and aqueous solutions of the salts of the invention are particularly preferred compositions.

Wetting agents, dispersing agents and emulsifying agents may be of the cationic, anionic or non-ionic type. Suitable agents of the cationic type include, for example, quaternary ammonium compounds, for example, cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodiu, calcium or ammonium lignosulphonate, butyl-naphthalene sulphonate, and a mixture of the sodium salts of diisopropyl- and triisopropylnaphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example polyvinyl-pyrrolidone and sodium carboxymethylcellulose, and the vegetable gums, for example gum acacia and gum tragacanth.

The aqueous dispersions or emulsions may be prepared by dissolving the active ingredient or ingredients in an organic solvent which may contain one or more wetting, dispersing or emulsifying agents and then adding the mixture so obtained to water which may likewise contain one or more wetting dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compositions to be used as sprays may also be in the form of aerosols wherein the formulation is held in a containiner under pressure in the presence of a propellant such as fluorotrichloromethane or dichlorodifuloromethane.

By the inclusion of suitable additives, for example for improving the distribution, adhesive power and resistance to rain on treated surfaces, the different compositions can be better adapted for the various uses for which they are intended.

The pyrimidine derivatives may also be conveniently formulated by admixing them with fertilizers. A preferred composition of this type comprises granules of fertilizer material incorporating, for example coated with a pyrimidine derivative. The fertilizer material may, for example, comprise nitrogen or phosphate containing substances.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 10–85% by weight of the active ingredient or ingredients and generally from 25–60% by weight of the active ingredient or ingredients. When diluted to form aqueous preparations, such preparations may contain varying amounts of the active ingredient or ingredients depending upon the purpose for which they are to be used, but an aqueous preparation containing between 0.001 and 10.0% by weight of active ingredient or ingredients may be used.

Particularly useful fungicidal compositions are those suitable for dressing seed and for spraying crops and examples hereinafter recite specific compositions suitable for these purposes. Thus aqueous solutions of hydrochlorides of the various active pyrimidine derivatives, optionally containing a wetting agent, are particularly useful as foliage spray formulations for crops, as are formulations of the well-known Ultra Low Volume (U.L.V.) type comprising a suspension of the active pyrimidine derivative in an inert organic liquid medium containing a surface active agent, and, if desired, a proportion of mineral oil.

It is to be understood that the fungicidal compositions of this invention may comprise, in addition to a pyrimidine derivative, one or more other compounds having biological activity.

Compositions according to the invention were made up in the following manner and tested against various fungal diseases, and the results of these tests are shown in Tables V to VIII hereinafter. In the tests, both a protectant and an eradicant test were carried out, and in the protectant test the plants were sprayed so that the leaves were wetted with a solution or suspension containing 500 parts per million of the active compound and 0.1% of a wetting agent, and after 24 hours were inoculated with the disease, the extent of which was was assessed visually at the end of the tests. In the eradicant tests, the plants were inoculated with the disease and then sprayed (so that the leaves were wetted) after a number of days depending on the disease with a solution or suspension containing 500 parts per million of the active compound and 0.1% of a wetting agents. The results are shown in Tables V to VIII as a grading giving the percentage amount of disease as follows. The time in days stated in the headings to the Tables is the period between spraying and assessment of the disease.

| Grading | Percentage Amount of Disease |
|---|---|
| 0 | 61 to 100 |
| 1 | 26 to 60 |
| 2 | 6 to 25 |
| 3 | 0 to 5 |

In Tables V to VII the letters A, B, C, D, E, F, G, H, I, and J, refer to the diseases listed below.

| Lettering | Disease |
|---|---|
| A | *Puccinia recondita* (Rust) |
| B | *Phytophthora infestans* (Late blight) |
| C | *Sphaerotheca fuliginea* (Powdery mildew) |
| D | *Erysiphe graminis* (Powdery mildew) |
| E | *Erysiphe graminis* (Powdery mildew) |
| F | *Podosphaera leucotricha* (Powdery mildew) |
| G | *Uncinula necator* (Powdery mildew) |
| H | *Plasmopara viticola* (Downy mildew) |
| I | *Piricularia oryzae* (Blast) |
| J | *Ventura inaequalis* (Scab) |

TABLE V

| | A | | B | | C | | D | | E | F | | G | H | I | J |
|---|---|---|---|---|---|---|---|---|---|---|---|---|---|---|---|
| | Wheat 10 days | | Tomato 4 days | | Cucumber 10 days | | Wheat 10 days | | Barley 10 days | Apple 7–14 days | | Vine 14 days | Vine 7 days | Rice 7 days | Apple 14 days |
| Compound No. | Prot | Erad | Prot | Erad | Prot | Erad | Prot | Erad | Prot | Prot | Erad | Prot | Prot | Prot | Prot |
| 1 | — | — | — | — | — | — | — | — | — | — | — | 2 | — | — | — |
| 2 | 0 | 0 | 1 | — | 3 | 3 | 3 | — | 3 | 3 | — | 1 | 1 | 0 | 0 |
| 3 | 3 | 0 | — | — | 3 | 3 | 0 | — | 3 | 3 | 1 | 0 | 3 | — | — |
| 4 | 3 | 0 | — | — | 3 | 3 | 3 | — | 3 | 3 | 3 | 1 | 0 | — | — |
| 5 | 2 | 0 | 1 | — | 3 | 1 | 2 | — | — | — | — | 0 | 3 | — | — |
| 6 | 0 | 0 | 1 | — | 3 | 3 | 1 | — | 1 | 1 | — | 0 | 2 | 0 | 1 |
| 7 | 0 | 0 | 0 | — | 2 | 1 | 1 | — | 3 | 0 | — | 1 | 3 | 3 | 1 |
| 8 | 0 | 0 | 1 | — | 0 | 0 | 1 | — | 0 | 0 | — | 0 | 3 | 0 | 0 |
| 9 | 0 | 0 | 2 | — | 3 | 3 | 2 | — | 3 | 1 | — | 0 | 2 | 2 | 1 |
| 10 | 0 | 1 | 2 | — | 0 | 0 | 0 | — | 0 | 1 | — | 0 | 3 | — | — |
| 11 | 0 | 1 | 3 | — | 0 | 0 | 0 | — | 0 | 0 | — | 0 | 3 | 0 | 1 |
| 12 | 0 | 0 | 0 | — | 3 | 3 | 2 | — | 1 | 3 | 3 | 0 | 3 | 1 | 0 |
| 13 | 0 | 0 | 1 | — | 0 | 3 | — | — | — | — | — | — | 0 | — | — |
| 14 | 0 | 0 | 1 | — | 3 | 3 | 1 | — | — | 2 | — | 0 | 3 | — | — |
| 15 | 0 | 0 | 2 | — | 0 | 2 | 0 | — | 0 | 2 | — | 0 | 3 | 0 | 0 |
| 16 | 0 | 0 | 0 | — | 0 | 3 | 0 | — | 0 | 2 | — | 0 | 3 | 2 | 2 |
| 17 | 0 | 0 | 1 | — | 3 | 1 | 2 | — | 0 | 0 | — | 0 | 3 | 2 | — |
| 18 | 0 | 0 | 0 | — | 0 | 0 | 0 | — | 0 | 1 | — | 0 | 3 | 1 | 1 |
| 19 | — | — | — | — | 2 | 0 | — | — | 0 | 0 | — | 0 | 1 | 0 | 1 |
| 20 | 0 | 0 | 1 | — | 2 | 3 | 1 | — | — | — | — | 2 | 2 | — | — |
| 21 | 0 | 0 | 2 | — | 3 | 3 | 0 | — | 1 | 1 | — | 0 | 0 | 1 | 0 |
| 22 | 0 | 0 | 3 | — | 0 | 0 | 1 | — | — | — | — | 1 | 2 | — | — |
| 23 | 0 | 0 | 0 | — | 3 | 3 | 1 | — | 3 | 2 | — | 0 | 1 | 1 | 0 |
| 24 | 0 | 0 | 1 | — | 0 | 0 | 1 | — | 0 | 1 | — | 2 | 2 | 2 | 1 |
| 25 | 0 | 0 | 0 | — | 3 | 3 | 0 | — | 2 | 0 | — | 0 | 2 | 2 | 1 |
| 26 | 0 | 0 | 1 | — | 0 | 0 | 0 | — | 3 | 0 | — | 0 | 3 | 0 | 0 |
| 27 | 0 | 0 | 0 | — | 3 | 3 | 3 | — | 0 | 3 | 3 | 0 | 2 | 1 | 2 |
| 28 | 0 | 0 | 2 | — | 3 | 3 | 3 | 1 | 3 | 0 | — | 1 | 0 | 3 | 0 |
| 29 | 1 | 0 | 2 | — | 2 | 3 | 2 | — | 3 | 0 | — | 0 | 1 | 0 | 0 |
| 30 | 0 | 0 | 2 | — | 3 | 3 | 3 | 1 | 3 | 3 | 3 | 0 | 1 | 0 | 1 |

TABLE V-continued

| Compound No. | A Wheat 10 days | | B Tomato 4 days | | C Cucumber 10 days | | D Wheat 10 days | | E Barley 10 days | F Apple 7-14 days | | G Vine 14 days | H Vine 7 days | I Rice 7 days | J Apple 14 days |
|---|---|---|---|---|---|---|---|---|---|---|---|---|---|---|---|
| | Prot | Erad | Prot | Erad | Prot | Erad | Prot | Erad | Prot | Prot | Erad | Prot | Prot | Prot | Prot |
| 32 | 0 | 0 | 0 | — | 1 | 0 | 0 | — | 0 | 0 | — | 1 | 2 | 0 | 0 |
| 33 | 3 | 0 | — | — | 2 | 2 | 3 | — | 3 | 2 | — | — | — | — | — |
| 34 | 0 | 0 | 1 | — | 3 | 3 | 2 | 1 | 3 | 2 | — | — | 0 | 1 | 0 |
| 35 | 0 | 0 | — | — | 3 | 3 | — | — | — | — | — | — | — | — | — |
| 37 | 0 | 0 | 3 | — | 3 | 3 | 2 | — | 3 | 3 | — | 0 | 1 | 0 | 1 |
| 38 | 0 | 0 | 3 | — | 3 | 1 | 1 | — | 1 | 1 | — | 0 | 0 | 0 | 2 |
| 39 | 3 | 0 | — | — | 1 | 0 | 0 | — | 0 | 0 | — | 0 | 0 | 1 | 0 |
| 40 | 1 | 0 | 0 | — | 3 | 3 | 2 | — | — | — | — | — | — | — | — |
| 41 | 0 | 0 | 1 | — | — | — | — | — | — | — | — | — | — | — | — |
| 43 | 2 | 0 | 0 | — | 0 | — | 0 | — | 1 | — | — | 0 | 1 | 2 | 1 |
| 44 | 0 | 0 | 0 | — | 0 | 0 | 0 | — | 0 | 1 | — | 1 | 0 | 1 | 0 |
| 45 | 0 | 0 | 0 | 0 | 0 | 0 | 0 | — | 2 | 0 | — | 0 | 3 | 0 | 0 |
| 46 | 0 | 0 | 0 | — | 0 | 0 | 0 | 0 | 0 | 0 | — | 0 | 0 | 0 | 1 |
| 47 | 2 | 0 | 1 | 0 | 3 | 3 | 0 | — | 0 | 0 | — | 1 | 0 | 0 | 0 |
| 48 | 0 | 0 | 0 | 1 | 0 | 0 | 2 | — | 3 | 3 | — | 2 | 0 | 3 | 1 |
| 49 | 0 | 0 | 0 | 1 | 0 | 1 | 3 | — | 0 | 0 | — | 3 | 2 | 3 | 0 |
| 50 | 0 | 0 | 0 | 0 | 0 | 0 | 1 | — | 0 | 3 | — | 0 | 2 | 1 | 0 |
| 51 | 0 | 0 | 0 | 0 | 1 | 0 | 2 | — | 0 | 1 | — | 0 | 2 | 2 | 0 |
| 52 | 0 | 0 | 0 | — | 0 | 0 | 2 | — | 1 | 1 | — | 0 | 0 | 1 | 1 |
| 53 | 0 | 0 | 0 | — | 0 | 0 | 0 | — | 0 | 1 | — | 1 | 1 | 2 | 0 |
| 54 | 0 | 0 | 0 | 0 | 3 | 1 | 3 | — | 1 | 1 | — | 0 | 1 | 2 | 0 |
| 55 | 0 | 0 | 0 | 0 | 0 | 0 | 0 | — | 0 | 1 | — | 0 | 1 | 3 | 0 |
| 56 | 0 | 0 | 0 | 0 | 0 | 1 | 0 | — | 1 | 0 | — | 0 | 1 | 3 | 1 |
| 57 | 0 | 0 | 0 | 0 | 0 | 0 | 1 | — | 1 | 2 | — | 0 | 0 | 1 | 0 |
| 58 | 0 | 2 | 3 | 0 | 0 | 1 | 1 | — | 2 | 0 | — | 2 | 3 | 1 | 2 |
| 59 | 0 | 0 | 3 | — | 0 | 0 | 0 | — | 0 | 1 | — | 0 | 1 | 3 | 0 |
| 60 | 0 | 0 | 0 | 0 | 0 | 1 | 0 | — | 0 | 0 | — | 0 | 0 | 3 | 1 |
| 61 | 0 | 0 | 0 | 0 | 0 | 1 | 0 | — | 0 | 2 | — | 0 | 2 | 3 | 0 |
| 62 | 0 | 0 | 0 | 0 | 3 | 3 | 3 | — | 3 | 0 | — | 1 | 3 | 0 | 0 |
| 63 | — | — | — | — | 3 | 1 | — | — | 13 | — | — | — | — | — | — |
| 64 | 3 | 3 | — | — | — | — | — | — | — | — | — | — | — | — | — |
| 65 | 0 | 0 | 0 | 0 | 3 | 3 | 0 | — | 2 | — | — | 1 | 0 | 0 | 0 |
| 66 | 0 | 0 | 0 | 0 | 3 | 3 | 1 | — | 3 | — | — | 0 | 1 | 0 | 0 |
| 67 | 0 | 0 | 0 | 0 | 3 | 3 | 0 | — | 0 | — | — | 0 | 0 | 3 | 3 |
| 68 | 1 | 0 | 0 | — | 0 | 0 | 0 | —0 | — | — | 0 | 0 | 0 | 0 | — |
| 69 | 1 | 0 | 0 | 0 | 3 | 2 | 0 | — | 1 | — | — | 0 | 3 | 0 | 3 |
| 70 | 0 | 0 | 0 | 0 | 3 | 3 | 3 | — | 3 | 3 | — | — | 3 | 1 | 0 |
| 71 | 0 | 0 | 0 | — | 0 | 0 | 0 | — | 2 | 2 | — | 0 | 1 | 3 | 1 |
| 72 | 0 | 0 | 0 | — | 0 | 0 | 0 | — | 0 | — | — | 0 | 0 | 0 | 0 |
| 73 | 0 | 0 | 2 | — | 0 | 0 | 1 | — | 3 | 1 | — | — | 0 | 0 | 1 |
| 74 | 1 | 0 | 0 | — | 0 | 0 | 1 | — | 0 | 0 | — | — | 2 | 1 | 0 |
| 75 | 0 | 0 | — | — | 3 | 3 | 3 | — | 3 | 1 | — | 3 | 2 | 1 | 0 |
| 76 | 0 | 0 | — | — | 3 | 3 | 3 | — | 3 | — | — | — | 1 | 1 | 0 |
| 77 | 3 | 0 | — | — | 2 | 3 | — | — | — | 3 | — | 3 | — | O | — |
| 79 | 0 | 0 | 0 | 2 | — | 0 | — | — | — | — | — | — | 2 | 3 | — |
| 80 | 0 | 0 | 1 | 0 | — | 0 | — | — | — | — | — | — | — | — | — |
| 81 | 0 | 0 | 0 | 0 | 0 | 0 | 0 | 0 | 0 | 0 | — | 0 | 0 | 2 | 1 |
| 82 | 0 | 0 | 1 | 0 | 0 | 0 | — | — | — | 0 | — | 0 | 0 | 3 | — |
| 83 | 0 | 0 | 0 | 0 | 0 | 0 | — | — | — | 0 | — | — | — | 3 | — |
| 84 | 1 | 0 | 2 | 0 | 0 | 2 | — | — | — | 3 | — | — | — | 0 | — |
| 85 | 0 | 0 | 0 | — | 0 | 0 | — | — | 0 | 0 | — | — | — | 0 | — |
| 86 | 0 | 0 | — | — | 0 | 0 | 1 | — | 0 | 3 | — | 0 | 1 | 3 | 2 |
| 87 | 0 | 0 | 0 | 0 | 0 | 0 | 2 | — | 0 | 3 | — | 0 | 3 | 3 | 0 |
| 88 | 0 | 0 | 0 | 1 | 0 | 1 | 0 | — | 0 | 0 | — | 0 | 1 | 0 | 3 |
| 89 | 0 | 0 | 1 | 0 | 0 | 1 | 0 | — | 0 | 0 | — | 0 | 0 | 0 | 3 |
| 90 | 0 | 0 | — | — | 3 | 3 | 2 | — | 3 | 1 | — | 0 | 0 | 0 | 3 |
| 91 | 1 | 1 | — | — | 3 | 3 | 3 | — | 3 | — | — | 2 | 2 | 0 | 0 |
| 100 | 0 | 0 | 0 | — | 2 | 0 | 3 | — | 0 | 1 | — | 0 | 3 | — | 1 |
| 101 | 2 | 0 | 1 | — | 3 | 0 | 0 | — | 0 | 0 | — | 2 | 0 | 0 | 0 |
| 102 | 0 | 0 | 0 | — | 0 | 0 | 1 | — | 1 | 2 | — | 3 | 3 | 2 | 0 |
| 103 | 0 | 0 | 0 | — | 0 | 1 | 0 | — | 0 | 0 | — | 3 | 3 | 1 | 0 |
| 104 | 2 | 0 | 2 | — | 0 | 1 | 0 | — | 2 | 0 | — | 1 | 3 | 1 | 2 |
| 105 | 0 | 0 | — | 0 | 3 | 3 | 0 | — | 0 | 1 | — | 1 | 0 | 0 | 0 |
| 106 | 1 | 0 | 0 | — | 0 | 0 | 0 | — | 1 | 0 | — | 2 | 2 | 2 | 2 |
| 107 | 0 | 0 | 3 | — | 0 | 0 | 0 | — | 0 | 0 | — | 1 | 3 | 1 | 2 |
| 108 | 0 | 0 | — | — | 2 | 0 | 0 | — | 0 | 2 | — | 1 | 1 | 1 | 0 |
| 109 | — | — | — | — | 3 | — | — | — | 2 | 1 | — | — | — | — | — |
| 110 | — | — | — | — | 3 | — | — | — | 3 | 3 | — | — | — | — | — |
| 111 | — | — | — | — | 3 | — | — | — | 3 | 3 | — | — | — | — | — |
| 112 | — | — | — | — | 3 | — | — | — | 2 | 3 | — | — | — | — | — |
| 113 | — | — | — | — | 3 | — | — | — | 3 | 3 | — | — | — | — | — |
| 114 | — | — | — | — | 3 | — | — | — | 3 | 3 | — | — | — | — | — |
| 115 | — | — | — | — | 3 | — | — | — | 3 | 3 | — | — | — | — | — |
| 116 | — | — | — | — | 3 | — | — | — | 3 | — | — | — | — | — | — |
| 117 | — | — | — | — | 3 | — | — | — | 3 | 3 | — | — | — | — | — |
| 118 | — | — | — | — | 3 | — | — | — | 3 | 1 | — | — | — | — | — |
| 119 | — | — | — | — | 3 | — | — | — | 3 | 3 | — | — | — | — | — |

TABLE VI

| Compound No. | A Wheat 10 days Prot | A Wheat 10 days Erad | B Tomato 4 days Prot | B Tomato 4 days Erad | C Cucumber 10 days Prot | C Cucumber 10 days Erad | D Wheat 10 days Prot | D Wheat 10 days Erad | E Barley 10 days Prot | F Apple 7–14 days Prot | F Apple 7–14 days Erad | G Vine 14 days Prot | H Vine 7 days Prot | I Rice 7 days Prot | J Apple 14 days Prot |
|---|---|---|---|---|---|---|---|---|---|---|---|---|---|---|---|
| 120 | 1 | 0 | 0 | — | 3 | 3 | — | — | 0 | 0 | — | 0 | 1 | 0 | 2 |
| 121 | 0 | 0 | 2 | — | 3 | 3 | — | — | — | — | — | — | — | — | — |
| 122 | 0 | 0 | 0 | — | 0 | 0 | 2 | — | 0 | 1 | — | 3 | 1 | 3 | 1 |
| 123 | 0 | 0 | 0 | — | 0 | 0 | 1 | — | 1 | 0 | — | 0 | 0 | 0 | 1 |
| 124 | 2 | 0 | 0 | — | 0 | 0 | 0 | — | 0 | 0 | — | 0 | 1 | 0 | 2 |
| 125 | — | — | — | — | 3 | — | — | — | 3 | 3 | — | — | — | — | — |
| 126 | — | — | — | — | 3 | — | — | — | — | 3 | — | — | — | — | — |

TABLE VII

| Compound No. | A Wheat 10 days Prot | A Wheat 10 days Erad | B Tomato 4 days Prot | B Tomato 4 days Erad | C Cucumber 10 days Prot | C Cucumber 10 days Erad | D Wheat 10 days Prot | D Wheat 10 days Erad | E Barley 10 days Prot | F Apple 7–14 days Prot | F Apple 7–14 days Erad | G Vine 14 days Prot | H Vine 7 days Prot | I Rice 7 days Prot | J Apple 14 days Prot |
|---|---|---|---|---|---|---|---|---|---|---|---|---|---|---|---|
| 127 | 0 | 0 | 0 | — | 3 | 3 | 0 | — | 1 | 1 | — | 0 | 0 | 0 | 0 |
| 128 | 1 | 0 | 0 | — | 3 | 3 | 0 | — | 0 | 1 | — | 0 | 0 | 0 | 0 |
| 129 | 1 | 0 | 0 | — | 3 | 3 | 2 | — | 0 | 3 | — | 1 | 2 | 2 | 2 |
| 130 | 2 | 0 | 0 | — | 3 | 0 | 3 | — | 3 | 3 | — | 0 | 0 | 3 | 2 |
| 131 | 1 | 1 | 0 | — | 0 | 1 | 3 | — | 3 | 3 | — | 0 | 0 | 3 | 1 |
| 132 | 1 | 0 | 0 | — | 3 | 2 | 3 | — | 3 | 3 | — | 0 | 1 | 1 | 1 |
| 133 | 1 | 0 | 0 | — | 2 | 1 | 0 | — | 0 | 1 | — | 2 | 0 | 2 | 0 |
| 134 | 0 | 0 | 0 | — | 0 | 0 | 0 | — | 3 | 2 | — | 0 | 2 | 1 | 1 |
| 135 | 0 | 0 | 0 | — | 1 | 1 | 0 | — | 3 | 2 | — | 0 | 0 | 0 | 1 |
| 136 | 0 | 0 | 0 | — | 0 | 1 | 0 | — | 0 | 3 | — | 2 | 2 | 3 | 3 |
| 137 | 0 | 0 | 0 | — | 0 | 0 | 1 | — | 0 | 3 | — | 0 | 2 | 1 | 2 |
| 138 | 0 | 0 | 1 | — | 1 | 0 | 0 | — | 1 | 0 | — | 0 | 1 | 0 | 0 |
| 139 | 1 | 0 | — | — | 2 | 2 | 3 | — | 3 | 3 | — | 0 | 0 | 0 | 3 |

TABLE VIII

| Compound No. | Sphaerotheca fuliginea (Powdery mildew) Cucumber 10 days Protectant | Erysiphe graminis (Powdery mildew) Barley 10 days Protectant | Podospharra leucotricha (Powdery mildew) Apple 7–14 days Protectant |
|---|---|---|---|
| 140 | 3 | 3 | 3 |
| 141 | 3 | 2 | 3 |
| 142 | 3 | 2 | 3 |
| 143 | 2 | 2 | 3 |
| 144 | 2 | 3 | 3 |
| 145 | 2 | 2 | 3 |
| 146 | 2 | 3 | 3 |
| 147 | 3 | 2 | 3 |
| 148 | 3 | 2 | 3 |
| 149 | 3 | 2 | 3 |
| 150 | 2 | 3 | 1 |
| 151 | 3 | 2 | 3 |
| 152 | 3 | 2 | — |
| 153 | 3 | 2 | 2 |
| 154 | 3 | 2 | 3 |
| 155 | 3 | 3 | 2 |
| 156 | 3 | 3 | 3 |
| 157 | 3 | 3 | 2 |
| 158 | 3 | 3 | 3 |
| 159 | 3 | 3 | 2 |
| 160 | 2 | 2 | 3 |
| 161 | 3 | 3 | 1 |
| 162 | 3 | 3 | 3 |
| 163 | 3 | 3 | 1 |
| 164 | 3 | 3 | 2 |
| 165 | 3 | 3 | 3 |
| 166 | 3 | 3 | 2 |
| 167 | 3 | 3 | 3 |

In a further test, pots of natural soil were treated with granules comprising, on a weight basis, 5% of active ingredient in the form of the compound numbered 4 in Table I above and 95% of Fuller's Earth granules. The preparation of these granules is described in Example 19 below. The amount of granules added to each pot was 0.16 grams.

Five wheat seeds were sown in each pot. A similar series was set up without granules. After 10 days all the pots were inoculated with mildew (*Erysiphe graminis*) by dusting with spores from infected plants. After a further 3 weeks the plants were assessed for mildew attack. Using a standard chart, the percentage leaf area infected was estimated as one of the following categories: 0, 1, 5, 25 50 and 100%. In the Table IX below, setting out the results of the tests, each figure represents the mean leaf area infected for the five plants in a pot.

TABLE IX

|  | Replicates % leaf area infected | | | | Mean |
|---|---|---|---|---|---|
| Pots and granules | 0 | 0 | 0 | 0 | 0 |
| Untreated pots | 50 | 50 | 50 | 35 | 46 |

In a further test cucumber plants liable to infestation with powdery mildew (*Sphaerotheca fuliginea*) were employed. These plants, growing in a glasshouse in beds or loam-based compost at a density of 2500 plants/acre, were treated once with a 0.01% solution of 2-dimethylamino-4-methyl-5-n-butyl-6-hydroxypyrimidine hydrochloride in water at a rate of 2.5 liters per plant. The plants remained free from mildew for 8 weeks. A second treatment was then carried out at the same rate, and mildew infection was held in check for a further seven weeks. Compared with controls, a yield increase of 20 cucumbers per plant was obtained.

Both the above tests were repeated using as the active ingredient the compounds numbered 2 to 6, 9, 12 17, 19 26 to 28, 30, 34, 37 to 40, 42, 47, 48, 54, 62 to 65, 67 70, 75 to 77, 90 to 92, 100, 101, 105, 120, 121, 127, 129, 130, 139 and good to excellent control of the mildew was obtained.

According to a further feature of the invention, we provide novel hydroxypyrimidines as listed and indicated as novel by an asterisk in Table I hereinabove.

Thus the invention provides in a further aspect, therefore, the following compounds:

5-n-butyl-2-cyanoamino-4-hydroxy-6-methylpyrimidine,
2-dimethylamino-4-hydroxy-6-methyl-5-n-pentylpyrimidine,
2-dimethylamino-4-hydroxy-6-methyl-5-n-propylpyrimidine,
2-dimethylamino-5-n-hexyl-4-hydroxy-6-methylpyrimidine,
5-n-butyl-4-hydroxy-6-methyl-2-pyrrolidinopyrimidine,
5-n-butyl-4-hydroxy-6-methyl-2-morpholinopyrimidine,
2-dimethylamino-4-ethyl-6-hydroxypyrimidine,
2-p-bromophenylamino-5-n-butyl-4-hydroxy-6-methylpyrimidine,
5-n-butyl-2-p-ethoxycarbonylphenylamino-4-hydroxy-6-methylpyrimidine,
5-n-butyl-4-hydroxy-6-methyl-2-p-tolylaminopyrimidine,
5-n-butyl-4-hydroxy-6-methyl-2-(4-methylpiperazinyl)pyrimidine,
5-benzyl-2-dimethylamino-4hydroxy-6-methylpyrimidine,
5-n-butyl-2-dimethylamino-4-hydroxy-6-phenylpyrimidine,
2-dimethylamino-4-hydroxy-6-methyl-5-isopropylpyrimidine,
5-n-butyl-4-hydroxy-6-methyl-2(3-morpholinopropylamino)pyrimidine,
5-n-butyl-2-dibenzylamino-4-hydroxy-6-methylpyrimidine,
5-n-butyl-4-hydroxy-6-methyl-2-ureidopyrimidine,
5-n-butyl-4-hydroxy-6-methyl-2(2-phenylhydrazino)pyrimidine,
4-hydroxy-6-methyl-2-piperidino-6-piperidinomethylpyrimidine,
5-n-butyl-2-di-n-butylamino-4-hydroxy-6-methylpyrimidine,
2-acetamido-5-n-butyl-4-hydroxy-6-methylpyrimidine,
5-n-butyl-2-isopropylamino-4-hydroxy-6-methylpyrimidine,
5-n-butyl-2-benzylamino-4-hydroxy-6-methylpyrimidine,
2-dimethylamino-4-ethylthiomethyl-6-hydroxypyrimidine,
2-dimethylamino-5-(2-ethyloxy)ethyl-4-hydroxy-6-methylpyrimidine,
5-n-butyl-2-dimethylamino-4-hydroxypyrimidines,
5-n-butyl-2-n-butylamino-4-hydroxy-6-methylpyrimidine,
2-dimethylamino-4-hydroxy-6-methyl-5-methylsulphonylpyrimidine
4-hydroxy-5-(1-hydroxy-2,2,2,-trichloroethyl)-6-methyl-2-methylaminopyrimidine,
2-allylamino-5-n-butyl-4-hydroxy-6-methylpyrimidine,
4,5-dimethyl-6-hydroxy-2-morpholinopyrimidine,
4-hydroxy-2-morpholino-6-n-propylpyrimidine,
4,5-dimethyl-6-hydroxy-2-piperidinopyrimidine,
2-dimethylamino-5-ethyl-4-hydroxy-6-methylpyrimidine,
2-dimethylamino-4-hydroxy-6-n-propylpyrimidines,
4-hydroxy-6-methyl-2-morpholino-5-n-propylpyrimidine,
5-n-butyl-4-hydroxy-6-methyl-2-piperidinopyrimidine,
2-dimethylamino-4hydroxy-6-phenylpyrimidine,
2-dimethylamino-4-hydroxy-5,6-trimethylenepyrimidine,
2-dimethylamino-4-hydroxy-6-methyl-5-n-octylpyrimidine,
2-dimethylamino-5-dimethylaminomethyl-4-hydroxy-6-methylpyrimidine,
2-dimethylamino-4-n-hexyl-6-hydroxypyrimidine,
5-n-butyl-4-hydroxy-6-methyl-2-n-propylaminopyrimidine,
5-isobutyl-2-dimethylamino-4-hydroxy-6-methylpyrimidine,
5-allyl-2-dimethylamino-4-hydroxypyrimidine,
2-dimethylamino-4-hydroxy-6-methyl-5-(3-methylbutyl)pyrimidine,
5-n-butyl-4-hydroxy-6-methyl-2-trifluoromethylcarbonylaminopyrimidine,
2-dimethylamino-5-ethyl-4-hydroxy-6-n-propylpyrimidine,
5-p-chlorophenylthio-2-dimethylamino-4-hydroxy-6-methylpyrimidine,
5-n-butyl-2-chloromethylcarbonylamino-4-hydroxy-6-methylpyrimidine,
5-n-butyl-2-dimethylamino-4-ethyl-6-hydroxypyrimidine,
2-dimethylamino-4-hydroxy-6-methyl-5-p-tolylthiopyrimidine,
5-benzylthio-2-dimethylamino-4-hydroxy-6-methylpyrimidine, 4-hydroxy-2-guanidino-6-methyl-5-n-propylpyrimidine,
5-n-butyl-2-ethylmethylamino-4-hydroxy-6-methylpyrimidine,
2-ethylmethylamino-4-hydroxy-6-methyl-5-n-propylpyrimidine,
2-diethylamino-4-hydroxy-6-methyl-5-n-propylpyrimidine,
5-allyl-4-hydroxy-6-methyl-2-m-nitrobenzenesulphonylaminopyrimidine,
2-acetamido-4-hydroxy-5-phenoxypyrimidine,
2-acetamido-4-hydroxy-5-phenylpyrimidine,
2-dimethylamino-5(3,4-dimethylbenzyl)-4-hydroxy-6-methylpyrimidine,
5-p-chlorobenzyl-2-dimethylamino-4-hydroxy-6-methylpyrimidine,
2-cyclohexylamino-4-hydroxy-6methyl-5-n-propylpyrimidine,
5(3,4-dichlorobenzyl)-2-dimethylamino-4-hydroxy-6-methylpyrimidine,
5(1-hydroxy-2,2,2-trichloroethyl)-4-hydroxy-2-morpholinopyrimidine,
5(1-hydroxy-2,2,2-trichloroethyl)-4-hydroxy-2(4-methylpiperazin-1-yl)pyrimidine,
5(1-hydroxy-2,2,2-trichloroethyl)-4-hydroxy-6-methyl-2-(pyrrolidin-1yl)pyrimidine,
2-ethylamino-5-(1-hydroxy-2,2,2-trichloroethyl)-4-hydroxypyrimidine,
2-diethylamino-5-ethyl-4-hydroxy-6-methylpyrimidine,
5-allyl-2-diethylamino-4-hydroxypyrimidine,
2-dimethylamino-5-ethyl-4-hydroxypyrimidine, 5-allyl-2-dimethylamino-4-hydroxy-6-phenylpyrimidine,
4-p-chlorophenyl-2-dimethylamino-6-hydroxypyrimidine,
2-dimethylamino-5-ethyl-4-hydroxy-6-phenylpyrimidine,
2-p-ethoxycarbonylanilino-4-hydroxy-6-methyl-5-n-propylpyrimidine,
2-p-chloroanilino-4-hydroxy-6-methyl-5-n-propylpyrimidine,
2-dimethylamino-4-hydroxy-5-p-methoxyphenylpyrimidine,
2-ethylamino-4-hydroxy-5-p-methoxyphenylpyrimidine,
$N^1$(4,5-dimethyl-6-hydroxypyrimidine) $N^3$-p-chlorophenyl guanidine,
4,10-bis(dimethylamino)6,8-dihydroxy-1,3,5-tetraazaanthracene.
4-hydroxy-6-methyl-2-tetrazolopyrimidine,
5-n-butyl-2-dimethylamino-4(2-hydroxyethyloxy)-6-methylpyrimidine,
5-n-butyl-4-(2-diethylaminoethyloxy)-2-dimethylamino-6-methyl pyrimidine,
6-benzyloxy-2-dimethylaminopyrimidine,
6-allyloxy-2-dimethylaminopyrimidine,
4,5-dimethyl-2-dimethylamino-6(2-hydroxyethyloxy)pyrimidine,
2-dimethylamino-4-mercapto-6-methylpyrimidine,
5-benzyl-2-ethylamino-4-hydroxy-6-methylpyrimidine,
2-ethylamino-4-hydroxy-6-methyl-5-n-pentylpyrimidine,
2-ethylamino-4-hydroxy-5-isoamyl-6-methylpyrimidine,
5-allyl-2-ethylamino-4-hydroxy-6-methylpyrimidine,
2-ethylamino-4-hydroxy-6-methyl-5-n-propylpyrimidine,
2-ethylamino-4-hydroxy-5-isobutyl-6-methylpyrimidine,
5-n-but-2-enyl-2-ethylamino-4-hydroxy-6-methylpyrimidine,
5-n-butyl-2-ethylamino-4-hydroxypyrimidine,
5-n-butyl-2-diethylamino-4-hydroxy-6-methylpyrimidine,
5-n-buty-2-enyl-2-dimethylamino-4-hydroxy-6-methylpyrimidine,
5-n-butyl-2-diallylamino-4-hydroxy-6-methylpyrimidine.

According to a further feature of the invention, we provide novel etherified hydroxypyrimidines as listed in Table II above. With the invention also we provide novel sulphur- containing pyrimidines of the general Formulae I and II, wherein X = S; in partiuclar, we provide the novel compounds listed in Table III above.

This invention further provides as new compounds salts of the pyrimidine derivatives hereinbefore defined, and in particular salts of the specific pyrimidines listed above both in the tables and by name, especially alkali metal salts and hydrochlorides.

The invention also provides a method of preparing hydroxypyrimidines having the general Formula I wherein the appropriate guanidine is condensed with a suitable substituted beta-ketoester, if necessary in the presence of a base.

The invention also provides a process for preparing hydroxy pyrimidines of the formula:

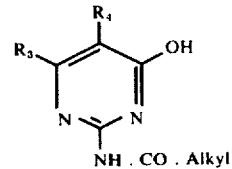

where $R_3$ and $R_4$ are as hereinbefore defined by acylating the corresponding 2-aminopyrimidine.

The invention also provides a method of preparing amino-hydroxypyrimidines by reacting the corresponding 2-alkylthiopyrimidine with the appropriate amine, for example as represented by the equation:

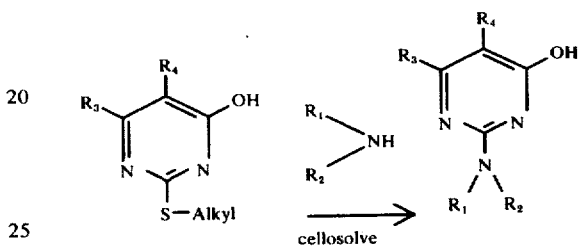

The 2-alkylthiopyrimidine is preferably a 2-methylthiopyrimidine.

Various other methods well-known to those skilled in the art may be used to prepare the fungicidally-active pyrimidine derivatives and in so far as these methods are pertinent to the preparation of new compounds they form part of the present invention. Techniques used to produce the pyrimidine derivatives include photochemical Claisen rearrangements, Mannich-type condensations and Schotten-Baumann reactions. The pyrimidine derivatives, where appropriate can be readily converted into the corresponding salts by usual methods, for example the corresponding sodium salt can be prepared by treating a pyrimidine derivative with sodium hydroxide and acid salts by treatment with the corresponding acid. Further examples of methods of preparing salts are set out in the examples recited subsequently and include, as separate or additional steps:
i. reacting the appropriate 6-halopyrimidine with an hydroxy compound to produce the corresponding 6-etherified pyrimidine derivative;
ii. reacting the appropriate 5-halopyrimidine with a mercaptan to form the corresponding 5-mercapto ether;
iii. hydrolysing the appropriate pyrimidine derivative containing a cyanamino group in position 2, thus preparing the corresponding 2-ureido derivative;
iv. reacting the appropriate 6-hydroxypyrimidine with phosphorus pentasulphide to produce the corresponding 6-mercapto derivative;
v. reacting the appropriate 6-mercapto pyrimidine derivative with the appropriate organic halide to obtain the corresponding thioether.

The invention is illustrated by the following Examples, those numbered 1–50 exemplifying methods of preparing the pyrimidine compounds listed in Tables I, II, III and IV above, while those numbered 51–71 are illustrative of fungicidal compositions containing various of the pyrimidines derivatives as active ingredient. In the latter group all references to percentage amounts of constituents are by weight and are based on the weight of the composition as a whole.

EXAMPLE 1

The hydroxypyrimidine having the formula:

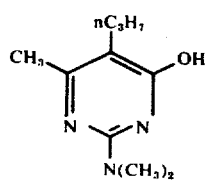

was prepared as follows:

To a solution of sodium (0.2 mole 4.6 g.) in dry methanol (120 ml.) was added askymmdimethylguanidine sulphate (0.1 mole, 27.2 g.) and the mixture was refluxed for 30 minutes. Ethyl n-propyl acetoacetate (0.2 mole, 34.4 g.) was added, and the reaction mixture refluxed with stirring for 20 hours. Water (100 ml.) was added to the cooled mixture, which was then neutralised with acetic acid and extracted exhaustively with methylene chloride. The methylene chloride solution was dried ($Na_2SO_4$), the solvent removed, and the crystalline residue recrystallised from ethanol (charcoal) to give needles, m.p. 120° (21 g., 54%).

The following compounds of Table I above were prepared by the above method:

| Compound Numbers | | | |
|---|---|---|---|
| 2 | 18 | 42 | 63 |
| 4 | 19 | 47 | 65 |
| 5 | 28 | 52 | 67 |
| 6 | 30 | 55 | 70 |
| 11 | 31 | 56 | 75 |
| 12 | 32 | 57 | 76 |
| 17 | 33 | 58 | 77 |
| | 34 | 60 | 82 |
| | | 62 | |
| | | 83 | 110 |
| | | 85 | 111 |
| | | 90 | 112 |
| | | 91 | 113 |
| | | 92 | 114 |
| | | 93 | 115 |
| | | 94 | 116 |
| | | 95 | 117 |
| | | 98 | 118 |
| | | 99 | 119 |
| | | 103 | |
| | | 106 | |
| | | 109 | |

EXAMPLE 2

The compound 5-n-Butyl-4-hydroxy-6-methyl-2-pyrrolidinopyrimidine, having the formula:

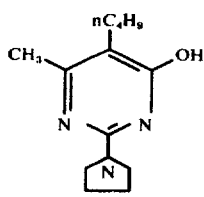

was prepared by the following method:

A mixture of 5-n-Butyl-4-hydroxy-6-methyl-2-methyl-thiopyrimidine (10.6 g., 0.05 mole), and pyrrolidine (17.75 g., 0.025 mole) in cellosolve (30 ml.) was refluxed for 16 hours. On cooling the product separated and was recrystallized from cellosolve to give colourless needles, m.p. 149° C., 9.8 g. (83%).

The compounds numbered 16, 20, 21, 25, 29, 44, 45, 46, 53, 54, 84, 96, 97 and 108 in Table I above were also prepared by the foregoing method using the appropriate reactants.

The compounds numbered 13, 14 and 15 were prepared in a similar manner, save that 48 hours were needed in order to complete the reaction.

EXAMPLE 3

The compound having the formula:

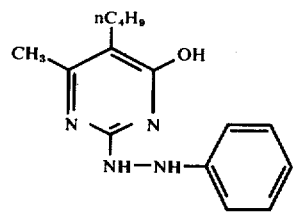

was prepared as follows:

A mixture of 5-n-Butyl-4-hydroxy-6-methyl-2-methyl-thiopyrimidine (5.3 g., 0.025 mole) and phenylhydrazine (20 ml., freshly distilled) was heated at 160° for 2 hours. On cooling the product separated, was filtered off, and recrystallised from ethanol to give colourless plates 1.5 g., m.p. 185° dec.

EXAMPLE 4

The compound having the formula:

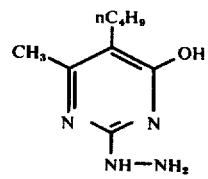

was prepared as follows:

A mixture of 5-n-butyl-4-hydroxy-6-methyl-2-methyl-thiopyrimidine (5.3 g., 0.025 mole), hydrazine hydrate (100%, 5 ml.) in absolute ethanol (20 ml.) was heated at 100° for 6 hours with exclusion of moisture. On cooling a solid separated which was filtered off, and washed with water. The crude product was purified by dissolving it in dilute hydrochloric acid, filtering, and neutralising the filtrate with sodium hydroxide solution to yield a white crystalline solid, (3 g.), m.p. 201°.

Compound No. 10, m.p. 192°–195°, was also prepared by the method of Example 4.

EXAMPLE 5

2-Acetylamino-5-n-butyl-4-hydroxy-6-methylpyrimidine having the formula:

was prepared as follows:

2-Amino-5-n-butyl-4-hydroxy-6-methylpyrimidine (10 g.) in acetic anhydride (40 c.c.) was refluxed for 2 hours, concentrated to dryness in vacuo, and the crude product taken up in 5% aqueous sodium hydroxide solution and re-precipitated with acetic acid. The material which separated was filtered off, washed with water, and recrystallised from aqueous ethanol, m.p. 153° (8.6 g., 70%). The following compounds were also prepared by the method of Example 5:- Compound numbers 66, 69, 79 and 81.

EXAMPLE 6

5-n-Butyl-2-cyanamino-4-hydroxy-6-methylpyrimidine having the formula:

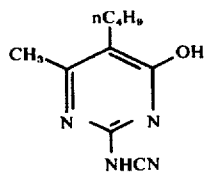

was prepared as follows:

Ethyl-n-butyl acetoacetate was condensed with dicyandiamide. The product was recrystallised from ethanol, m.p. 295°–298° dec.

EXAMPLE 7

5-n-Butyl-4-hydroxy-6-methyl-2-ureidopyrimidine having the formula:

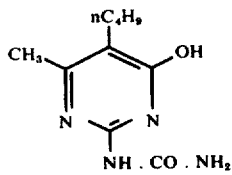

was prepared by the hydrolysis of 5-n-Butyl-2-cyanamino-4-hydroxy-6-methylpyrimidine with 10% aqueous hydrochloric acid under reflux for 1 hour, to give the above product, m.p. 207° after recrystallization from water.

EXAMPLE 8

5-n-Butyl-4-(2-diethylaminoethoxy)-2-dimethylamino-4-methylpyrimidine having the formula:

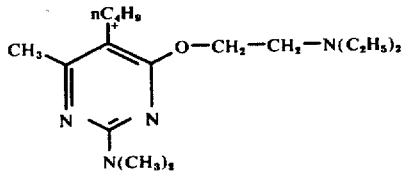

was prepared as follows:

Sodium (0.46 g., 0.02 mole) was dissolved in 2-diethylaminoethanol (30 g.). To the solution was added 5-n-butyl-4-chloro-2-dimethylamin-6-methylpyrimidine (0.02 mole), and the reaction mixture stirred at 130°–140° for 3 hours. Excess of 2-diethylaminoethanol was removed in vacuo, and the residue dissolved in a mixture of methylene chloride and water. The methylene chloride layer was dried (Na$_2$SO$_4$), and the solvent removed. Distillation gave the product, b.p. 126°/0.23 mm. n$_D^{23}$ = 1.5046.

By a similar method there was also prepared compound numbered 120 having b.p. 126°/0.4 mm., n$_D^{20}$ = 1.5250; also compounds numbered 122, to 126 inclusive.

EXAMPLE 9

5-n-Butyl-2-dimethylamino-4-mercapto-6-methylpyrimidine having the formula:

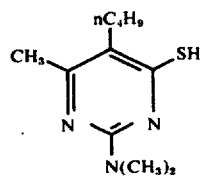

was prepared as follows:

A mixture of 5-n-butyl-2-dimethylamino-4-hydroxy-6-methylpyrimidine (58 g.) and phosphorus pentasulphide (110 g.) in xylene (550 ml.) was refluxed for 6 hours.

The mixture was cooled, the xylene decanted and the residue extracted with 5% aqueous sodium hydroxide solution. The alkaline extract was filtered, and the filtrate cooled and acidified to pH 6.0 with glacial acetic acid. The solid obtained was filtered off, and recrystallised from ethanol - water (charcoal) to give the product, 50 g., m.p. 104°–105° C.

In a similar manner compound numbered 129 having a m.p. of 140°–141° was obtained; also compounds numbered 127, 134, 136 and 137.

EXAMPLE 10

5-n-Butyl-2-dimethylamino-4-(2-dimethylaminoethyl)thio-6-methylpyrimidine having the formula:

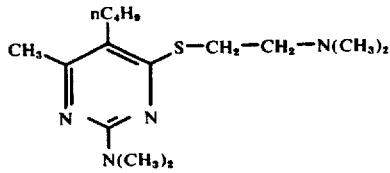

was prepared as follows:

To a mixture of 2-dimethylaminoethyl chloride hydrochloride (5.76 g., 0.04 mole) and 5-n-butyl-2-dimethylamino-4-mercapto-6-methylpyrimidine (4.5 g., 0.02 mole) in water (50 ml.) was added slowly at room temperature 10N aqueous sodium hydroxide solution extracted with chloroform. The chloroform extract was washed with water, dried (Mg SO$_4$), and the solvent removed. Distillation gave the product, b.p. 152°–153°/0.23 mm., n$_D^{25}$ = 1.5452.

In a similar manner was prepared the compound numbered 131 having b.p. 160°/0.33 mm., n$_D^{25}$ = 1.5670; also compounds numbered 128, 132, 135, 138 and 139.

EXAMPLE 11

The compound 5-Allyl-2-dimethylamino-4-hydroxpyrimidine having the formula:

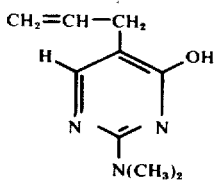

was prepared as follows:

A solution of 4-allyloxy-2-dimethylamiopyrimidine (1 g.) in dry ethanol (75 ml.) was placed in a quartz flask and irradiated with an Ultraviolet lamp for 16 hours. The solvent was then removed in vacuo and the residue taken up in petroleum ether and chromatographed using a column (1 cm. × 20 cm.) of silica gel. The product (200 mg.) was eluted from the coliumn by means of chloroform. Recrystallization from a small quantity of ethanol gave needles, m.p. 94° C. Compound Number 37 was prepared by an analogous method.

EXAMPLE 12

The compound 2-guanidino-4-hydroxy-6-methyl-5-n-propyl pyrimidine, having the formula:

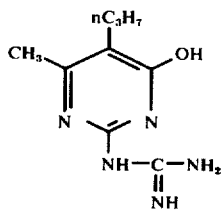

was prepared as follows;

Sodium hydroxide solution (11N, 40 ml., 0.44 mole) was added in portions to a stirred and cooled suspension of biguanide sulphate (43.4 g.) in ethanol (50 ml.), keeping the temperature below 10° C. The mixture was stirred for 5 minutes, ethyl α-n-propylacetoacetate (37.8 g., 0.22 mole) was added in portions below 10° C. and the mixture was stirred at room temperature for 18 hours. The resulting suspension was filtered and the residue washed with ethanol. The residue was shaken with 200 ml. water, filtered, washed with cold water (4 ml. × 50 ml.) and dried at 100° C. Yield, 45 g., m.p. 291°–293° C.

EXAMPLE 13

The compound 5-allyl-4-hydroxy-6-methyl-2(m-nitro benzenesulphonamido)pyrimidine, having the formula:

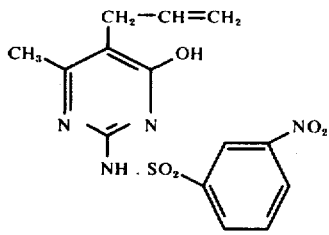

was prepared as follows:

5-Allyl-2-amino-4-hydroxy-6-methyl-pyrimidine (4.96 g., 0.03 mole) was suspended in dry dimethylformamide (40 ml.). To the suspension was added m-nitrobenzene sulphonylchloride (6.66 g., 0.03 mole) and the mixture was stirred at room temperature. A solution of triethylamine (3.09 g., 0.03 mole) in dimethylformamide (5 ml.) was added dropwise; the reaction mixture was stirred for 2 hours and poured on to water (250 ml.). The mixture was allowed to stand at 0° C overnight, and the product filtered off, dried, and recrystallised from methanol. Yield, 4.2 g., m.p. 233°–234° C.

EXAMPLE 14

The compound 2-dimethylamino-5-dimethylaminomethyl-4-hydroxy-6-methylpyrimidine hydrochloride, having the formula:

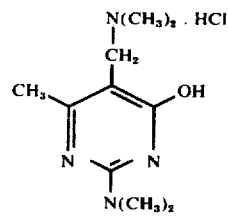

was prepared as follows:

A mixture of 2-dimethylamino-4-hydroxy-6-methylpyrimidine (15.3 g., 0.1 mole), 37% formalin (0.1 mole) and dimethylamine hydrochloride, (7.8 g., 0.1 mole) in ethanol (70 ml.) was refluxed for 2 hours. The solution was filtered hot and allowed to cool. The product (9.2 g.) was filtered off, sucked dry, and recrystallised from ethanol, m.p. 280°–290° C.

EXAMPLE 15

The hydroxypyrimidine having the formula:

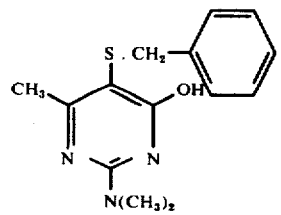

was prepared as follows:

To a solution of sodium (0.04 mole, 0.92 g.) in ethanol (15 ml) in an atmosphere of nitrogen was added benzyl mercaptan (0.04 mole, 5 g.) and the whole mixture was stirred for 5 minutes at room temperature. Then ethane -1,2 diol (90 ml.) and 5-bromo-2-dimethylamino-4-hydroxy-6-methylpyrimidine (0.044 mole, 10.1 g.) were added and the whole stirred for 5 hours at 140° C. Thereafter the reaction mixture was cooled and poured into water (500 ml.), brought to pH 6.0–7.0 with acetic acid to give the product, m.p. 175°–176°, after recrystallisation from ethanol. Compounds numbered 68 to 71 were similarly prepared using the appropriate reactants.

EXAMPLE 16

This example illustrates the preparation of the hydrochloride of 2-dimethylamino-4-methyl-5-n-butyl-6- hydroxy-pyrimidine (Compound No. 4 of Table I). 2-Dimethylamino-4-methyl-5-n-butyl-6-hydroxypyrimidine (10 g.) was mixed thoroughly with concentrated hydrochloric acid of specific gravity 1.18.

There was thereby obtained a powder comprising 2-dimethylamino-4-methyl-5-n-butyl-6-hydroxypyrimidine hydrochloride (11.7 g.). This was recrystallised using isopropyl alcohol benzene and gave a melting point of 167° C.

In exactly the same manner the hydrochloride of 2-ethylamino-4-methyl-5-n-butyl-6-hydroxypyrimidine (Compound No. 30 of Table I) was prepared.

EXAMPLE 17

This example illustrates the preparation of an aqueous solution of the hydrochloride of 2-dimethylamino-4-methyl-5-n-butyl-6-hydroxypyrimidine (Compound No. 4 of Table I). 2-Dimethylamino-4-methyl-5-n-butyl-6-hydroxypyrimidine (10 g.) were added to water (10 ml.) and concentrated hydrochloric acid was added (3.8 g.). The resultant mixture was then warmed to 50° C and held at this temperature until a clear solution was obtained. After cooling, water (40 ml.) was added and the solution then contained 29.3% by weight of 2-dimethylamino-4-methyl-5-n-butyl-6-hydroxypyrimidine in the form of the hydrochloride thereof.

In exactly the same manner an aqueous solution of the hydrochloride of 2-ethylamino-4-methyl-5-n-butyl-6-hydroxypyrimidine (Compound No. 30 of Table I) was prepared.

EXAMPLE 18

This example illustrates the preparation of an aqueous solution of the citric acid salt of 2-dimethylamino-4-methyl-5-n-butyl-6-hydroxypyrimidine (Compound No. 4 of Table I). 2-Dimethylamino-4-methyl-5-n-butyl-6-hydroxypyrimidine (10 g.) is dissolved in water (30 ml.) and nitric acid added (4.3 g. of a 70% w/v solution). The mixture was warmed until all the solid had dissolved and then water (100 ml.) added to yield a solution containing 13.1% w/v of 2-dimethylamino-4-methyl-5-n-butyl-6-hydroxypyrimidine in the form of the nitric acid salt thereof.

EXAMPLE 19

In a similar manner to that described in Example 18 aqueous solutions of the sulphuric acid and phosphoric acid salts, respectively, of 2-dimethylamino-4-methyl-5-n-butyl-6-hydroxypyrimidine were obtained, using corresponding amounts respectively, of sulphuric acid and phosphoric acid instead of nitric acid. The resultant solutions contained 12.3% w/v and 14.7% w/v respectively, of the sulphuric and phosphoric acid salts of 2-dimethylamino-4-methyl-5-n-butyl-6-hydroxypyrimidine.

EXAMPLE 20

This example illustrates the preparation of the potassium salt of 2-dimethylamino-4-methyl-5-n-butyl-6-hydroxypyrimidine (Compound No. 4 of Table I).

2-Dimethylamino-4-methyl-5n-butyl-6-hydroxypyrimidine (4 g.) was dissolved in absolute ethanol (30 ml.) with warming and the resultant solution added to a solution of potassium hydroxide (1.16 g.) in absolute ethanol (25 ml.). The mixture was stirred for one hour at room temperature and the solvent then evaporated off leaving a white solid which was dried at 100° C. over phosphorus pentoxide. The solid was the potassium salt of 2-dimethylamino-4-methyl-5-n-butyl-6-hydroxypyrimidine, m.p. 310°–316° C. (with decomposition).

EXAMPLE 21

This example illustrates the preparation of the sodium salt of 2-dimethylamino-4-methyl-5-n-butyl-6-hydroxypyrimidine (Compound No. 4 of Table I).

2-Dimethylamino-4-methyl-5-n-butyl-6-hydroxypyrimidine (4 g.) was dissolved in absolute ethanol (30 ml.) with warming and the resultant solution added to a solution of metallic sodium (0.44 g.) in absolute ethanol (25 ml.). The mixed solutions were warmed to 50° C. for 1 hour whereafter the solvent was removed by evaporation leaving a white solid consisting of the sodium salt of 2-dimethylamino-3-methyl-5-n-butyl-6-hydroxypyrimidine which was dried at 100° C. over phosphorus pentoxide, m.p. 285° C (with decomposition).

EXAMPLE 22

This example illustrates the preparation of the p-toluene sulphonate salt of the compound 5-n-butyl-2-dimethylamino-4-hydroxy-6-methylpyrimidine.

To a hot solution of 5-n-butyl-2-dimethylamino-4-hydroxy-6-methylpyrimidine (2.09 g., 0.01 mole) in ethanol (15 ml.) was added p-toluenesulphonic acid (1.60 g., 0.01 mole). The solution was heated under reflux for 30 seconds, filtered rapidly and the filtrate allowed to cool, whereupon the p-toluenesulphonate salt of the pyrimidine separated, m.p. 148° C.

EXAMPLE 23

This example illustrates the preparation of the fluoroborate of the compound 5-n-butyl-2-dimethylamino-4-hydroxy-6-methylpyrimidine.

The pyrimidine derivative (2.09 g., 0.01 mole) was added to an aqueous solution of fluoroboric acid (10 ml. of N solution; 0.01 mole) and the mixture warmed to 70° C. to bring about solution. On cooling, colourless crystals, m.p. 122°–123°, separated.

EXAMPLE 24

This example illustrates the preparation of the hydrobromide of the compound 5-n-butyl-2-dimethylamino-4-hydroxy-6-methylpyrimidine.

To a solution of the pyrimidine derivative (2.09 g., 0.01 mole) in acetic acid (10 ml.) was added a solution of hydrogen bromide in acetic acid (2 ml. of 45% w/v solution). The solvent was removed in vacuo and the residue was triturated with petroleum ether. The crystalline product was filtered off and dried, m.p. 184°–186° C.

EXAMPLE 25

This example illustrates the preparation of the thiocyanate of the compound 5-n-butyl-2-dimethylamino-4-hydroxy-6-methylpyrimidine.

To a solution of the pyrimidine derivative (2.09 g., 0.01 mole) in N hydrochloric acid (10 ml.) was added a solution of potassium thiocyanate (0.97 g., 0.01 mole) in water (5 ml.). The mixture was warmed briefly and filtered. On cooling, the thiocyanate salt separated, m.p. 129°–130° C.

EXAMPLE 26

This example illustrates the preparation of di-(5-n-butyl-2-dimethylamino-4-hydroxy-6-pyrimidinyl) mercury.

5-n-butyl-2-dimethylamino-4-methyl-6-hydroxypyrimidine (2.09 g., 0.01 mole) was dissolved in N sodium hydroxide solution (10 ml.) by gently warming on the steam bath. To this solution was added a solution of mercuric chloride (1.37 g., 0.005 mole) in water (10 ml.) and ethanol (5 ml.). A white precipitate was formed immediately, and this rapidly turned light brown. The mixture was diluted with water, and the product filtered off, washed with water, ethanol, and ether, and finally dried, m.p. 202°–205° C. (decomposition).

EXAMPLE 27

This example illustrates the preparation of the silver salt of the compound 5-n-butyl-2-dimethylamino-4-methyl-6-hydroxypyrimidine.

To a solution of the pyrimidine derivative (2.09 g., 0.01 mole) in N sodium hydroxide solution (10 ml.) was added an aqueous solution of silver nitrate (0.01 mole). The precipitated silver salt was filtered off, washed with water, ethanol, and ether and dried, m.p. 190°–194° C. (decomposition).

EXAMPLE 28

This example illustrates the preparation of the mercurichloride of the compound 5-n-butyl-2-dimethylamino-4-methyl-6-hydroxypyrimidine.

To a solution of the pyrimidine derivative (2.09 g., 0.01 mole) in N sodium hydroxide solution (10 ml.) was added with vigorous stirring a saturated solution of mercuric chloride (2.71 g., 0.01 mole) in ethanol. The brown precipitate which formed was filtered off after 10 minutes, washed with water, ethanol, and ether, and dried., m.p. 250°–255° C. (softens 180°).

EXAMPLE 29–33

In a similar manner to the methods elucidated above the following further salts of the compound 2-dimethylamino-4-methyl-5-n-butyl-6-hydroxypyrimidine were prepared.

| Example No. | Salt | Physical Characteristics. |
|---|---|---|
| 29 | Oxalate | m.p. 132° C |
| 30 | 2,4,6-trinitrobenzenesulphonate | m.p. 209–210° C. |
| 31 | 3,5-dinitrobenzoate | m.p. 159° C. |
| 32 | Trichloroacetate | m.p. 95° C. |
| 33 | Picrate | m.p. 182–183° C. |

EXAMPLE 34–47

By using methods similar to those described in the preceding examples the following salts of the compound 2-ethylamino-4-methyl-5-n-butyl-6-hydroxypyrimidine were prepared:

| Example No. | Salt | Melting Point |
|---|---|---|
| 34 | Acid oxalate | 182° C |
| 35 | Oxalate | 162–164° C |
| 36 | p-toluenesulphonate | 187° C |
| 37 | 2,4,6-trinitrobenzene sulphonate | 215–218° C |
| 38 | Trichloroacetate | 118° C (with decomposition) |
| 39 | Citrate | 154° C |
| 40 | Picrate | 247–249° C |
| 41 | Hydrochloride | 173–174° C |
| 42 | Hydrobromide | 201–202° C |
| 43 | Perchlorate | 96–97° C. |
| 44 | Thiocyanate | 186–188° C |
| 45 | Pyrimidinyl-mercurichloride | 201° C (with decomposition) |
| 46 | Di-pyrimidinyl-mercury | 232–234° C. |
| 47 | Silver | 250–255° C (with decomposition) |

EXAMPLE 48

The compound 2-dimethylamino-5-dimethylaminomethyl-4-hydroxy-6-methylpyrimidine hydrochloride, having the formula:

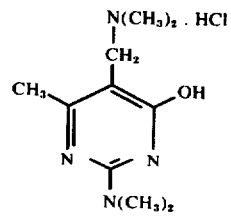

was prepared as follows:

A mixture of 2-dimethylamino-4-hydroxy-6-methylpyrimidine (15.3 g., 0.1 mole), 37% formalin (0.1 mole) and dimethylamine hydrochloride, (7.8 g., 0.1 mole) in ethanol (70 ml.) was refluxed for 2 hours. The solution was filtered hot and allowed to cool. The product (9.2 g.) was filtered off, sucked dry, and recrystallised from ethanol, m.p. 280°–290° C.

EXAMPLE 49

This example illustrates the preparation of a water-soluble powder comprising 50% by weight of the hydrochloride of Compound No. 4 of the Table I as the active ingredient.

The entire amount of the product produced by the method of Example 16 was ground together with potassium chloride (6.2 g.) to yield a powder which dissolves rapidly in water.

EXAMPLE 50

This example illustrates the preparation of a soluble powder comprising the potassium salt of Compound No. 4 of Table I as the active ingredient. The potassium salt of 2-dimethylamino-4-methyl-5-n-butyl-6-hydroxypyrimidine (2.47 g.), prepared according to Example 20, was mixed and ground with potassium sulphate (1.53 g.) to yield a powder which dissolves rapidly in water.

In the following Examples the words: "LUBROL", "AROMASOL", "DISPERSOL", "LISSAPOL", "CELLOFAS" are Trade Marks. Their constitution, unless indicated, is as follows:

| | |
|---|---|
| "LUBROL"L | A dispersing agent which is condensate of 1 mole of nonyl phenol with 13 molar proportions of ethylene oxide. |
| "AROMASOL" H | A solvent comprised of a mixture of aromatic hydrocarbons, mainly the three isomeric trimethylbenzenes S.F. 0.875 to. 0.885. Boiling Range 160° C to 210° C. |
| "LISSAPOL NX" | A wetting agent which is a condensate of 1 mole of nonyl phenol with 8 moles of ethylene oxide. |
| "DISPERSOL T" | A mixture of sodium sulphate and a condensate of formaldehyde with the sodium salt of naphthalene sulphonic acid. |
| "CELLOFAS" B600 | A sodium carboxymethyl cellulose thickener. |
| "LUBROL" APN 5" | A condensate of 1 mole of nonylphenol with 5½ moles of naphthalene oxide. |

EXAMPLE 51

An emulsion concentrate was made up by mixing together the ingredients set out below in the proportions stated and stirring the mixture until all the constituents were dissolved.

| | |
|---|---|
| Compound No. 4 | 10% |
| Ethylene dichloride | 40% |
| Calciumdodecylbenzenesulphonate | 5% |
| "Lubrol" L | 10% |
| "Aromasol" H | 35% |

EXAMPLE 52

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44-100, to obtain the desired size of grains.

| | |
|---|---|
| Compound No. 4 | 50% |
| "Dispersol" T | 25% |
| "Lubrol" APN 5 | 1.5% |
| Sodium Acetate | 23.5% |

EXAMPLE 53

The ingredients listed below were all ground together in the porportions stated to produce a powder formulation readily dispersible in liquids.

| | |
|---|---|
| Compound No. 4 | 45% |
| "Dispersol" T | 5% |
| "Lissapol" NX | 0.5% |
| "Cellofas" B600 | 2% |
| Sodium acetate | 47.5% |

EXAMPLE 54

The active ingredient (Compound No. 4 of Table I) was dissolved in a solvent and the resultant liquid was sprayed onto the granules of Fuller's earth. The solvent was then allowed to evaporate to produce a granular composition.

| | |
|---|---|
| Compound No. 4 | 5% |
| Fuller's earth or China clay granules | 95% |

EXAMPLE 55

A composition suitable for use as a seed dressing was prepared by mixing all three of the substituents set out below in the proportions stated.

| | |
|---|---|
| Compound No. 4 | 50% |
| Mineral oil | 2% |
| China clay | 48% |

EXAMPLE 56

A dusting powder was prepared by mixing, in the porportions stated, the active ingredient with talc.

| | |
|---|---|
| Compound No. 4 | 5% |
| Talc | 95% |

EXAMPLE 57

A Col formulation was prepared by ball-milling the constituents set out below and then forming an aqueous suspension of the ground mixture with water.

| | |
|---|---|
| Compound No. 4 | 40% |
| "Dispersol" | 10% |
| "Lubrol" | 1% |
| Water | 49% |

EXAMPLE 58

Formulations similar to those set out in Examples 51–57 above but containing as active ingredient a compound numbered 2, 3, 9, 12, 28, 30, 37, 62, 70, 75, 91, 117, 129, 130, or 139, respectively, from Tables I, II and III above, were prepared by methods similar to those described in each particular Example

EXAMPLE 59

This example illustrates the preparation of a fungicidal composition in the form of an aqueous solution containing 1.2% by weight of the salt prepared in Example 20.

The potassium salt of 2-dimethylamino-4-methyl-6-n-butyl-6-hydroxypyrimidine (2.47 g.) prepared according to Example 20 is dissolved in water (200 ml.).

EXAMPLE 60

This example illustrates the preparation of a fertiliser composition comprising as active ingredient the salt of 2-ethylamino-4-methyl-5-n-butyl-6-hydroxypyrimidine. The active ingredient was dissolved in trichloroethylene and the "TRILAC" added to this solution. The mixed solutions were then sprayed onto the fertiliser and the trichloroethylene was evaporated off. The proportions of the constituents in the product were as follows:

| | |
|---|---|
| I C I No. 2 Fertiliser | 97.9% |
| Potassium Salt of Compound No. 30 (Table I) | 0.3% |
| "TRILAC" (registered Trade Mark) a solution of an alkyl resin | 1.8% |

EXAMPLE 61

An emulsion concentrate was made up by mixing together the ingredients set out below in the proportions stated and stirring the mixture until all the constituents were dissolved.

| | |
|---|---|
| Calciumdodecylbenzenesulphonate salt of Compound No. 4 | 15% |
| Ethylene Dichloride | 40% |
| 'LUBROL' L | 10% |
| 'AROMASOL' H | 35% |

EXAMPLE 62

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44–100, to obtain the desired size of grains.

| | |
|---|---|
| Potassium salt of Compound No. 4 | 50% |
| 'DISPERSOL' T | 25% |
| 'LUBROL' APN5 | 1.5% |
| Sodium acetate | 23.5% |

EXAMPLE 63

The ingredients listed below were all ground together in the proportions stated to produce a powder formulation readily dispersible in liquids.

| | |
|---|---|
| Hydrochloride of Compound No. 4 | 45% |
| 'DISPERSOL' T | 5% |
| 'LISSAPOL' NX | 0.5% |
| 'CELLOFAS' B600 | 2% |
| Sodium acetate | 47.5% |

EXAMPLE 64

The active ingredient (Potassium salt of Compound No. 4 of Table I) was dissolved in a solvent and the resultant liquid was sprayed onto the granules of Fuller's earth. The solvent was then allowed to evaporate to produce a granular composition.

| | |
|---|---|
| Potassium salt of Compound No. 4 | 5% |
| Fuller's earth or China clay granules | 95% |

EXAMPLE 65

A composition suitable for use as a seed dressing was prepared by mixing all three of the constituents set out below in proportions stated.

| | |
|---|---|
| Potassium salt of Compound No. 4 | 50% |
| Mineral Oil | 2% |
| China Clay | 48% |

EXAMPLE 66

A dusting powder was prepared by mixing, in the proportions stated, the active ingredient with talc.

| | |
|---|---|
| Hydrochloride of Compound No. 4 | 5% |
| Talc | 95% |

EXAMPLE 67

This Example illustrates a spray formulation.

| | | |
|---|---|---|
| Compound No. 30 | | 20% |
| 'TRITON B 1956' | (an ethoxylated alkyd resin - Rohm & Haas) | 5% |
| 'AROMAS' T | (a mixture of C$_{10}$ aromatic hydrocarbons bp. 187° to 211° C) | 33% |
| Mineral Oil | | 21% |
| 'ISOPAR' G | (a mixture of aliphatic C$_{10}$–C$_{12}$ | |

| | |
|---|---|
| hydrocarbons - Esso) | to 100% |

The active compound and the other ingredients were all wet-milled together to form a suspension suitable for spray usage without further dilution.

EXAMPLE 68

This Example illustrates a spray formulation:

| | |
|---|---|
| Compound No. 30 | 10% |
| Hydrochloric acid (S.G. 1.18) | 8% |
| Water | to 100% |

The active compound was dissolved in the hydrochloric acid and the solution then diluted with water. This spray formulation is further diluted for use as a plant spray.

EXAMPLE 69

This Example illustrates a sprayable liquid which is diluted with water before use as a foliage spray formulation:

| | |
|---|---|
| Compound No. 30 | 10% |
| Hydrochloric acid (concentrated S.G. 1.18) | 8% |
| 'LUBROL' W | 5% |
| Water | to 100% |

The active compound is dissolved in the hydrochloric acid with warming and the solution filtered before adding in the 'Lubrol' W and diluting with water.

EXAMPLE 70

This Example illustrates a spray formulation:

| | |
|---|---|
| Compound No. 30 | 10% |
| Hydrochloric Acid (S.G. 1.18) | 8% |
| 'LUBROL' W | 5% |
| 'NATROSOL' 250L | 1% |
| Water | to 100% |

The preparation is the same as that for Example 69 except that the 'Natrosol' is added with the 'Lubrol' W. This formulation is diluted with water for use.

EXAMPLE 71

This Example illustrates a spray formulation:

| | |
|---|---|
| Compound No. 30 | 10% |
| Hydrochloric acid (S.G. 1.18) | 8% |
| Glycerol | 70% |
| Water | to 100% |

The active compound is dissolved in the hydrochloric acid and the solution filtered before adding the glycerol and further diluting with water.

This formulation is further diluted with water before use as a foliage spray.

The various emulsifiers and dispersing, wetting and surface active agents specified above are referred to and described in McCutcheon's Detergent and Emulsifier Annual over the last 5 to 10 years.

The amount of active pyrimidine compound which needs to be used to produce a useful fungicidal effect can vary widely. In general there is no upper limit other than that dictated by economy and the avoidance of the production of undesired phytotoxic effects. However the concentration of active pyrimidine compound ultimately attained in the leaves of a treated plant should be at least 0.05 ppm in order to obtain a substantial effect, whether the compound is applied in one or a plurality of applications. The optimum amount of active compound used in any instance will depend upon a number of factors, not least the efficacy, solubility and persistence of the particular compound selected. Other factors influencing the optimum amount of compound are the type of formulation used and its mode of application.

In general with the more active compounds as illustrated by the study of Tables V to IX and pages 42 and 43 it has been found necessary to apply a sufficient amount of the active compound to produce a concentration of that compound in the leaf tissue of the plant being treated of about 0.05 to 0.1 ppm. Depending upon the mode of application the formulation used needs to contain a substantially greater concentration of the active compound in order to ensure that this latter concentration in the leaf tissue is reached. The concentration for the formulation applied therefore needs to be considerably higher, usually at least 5 ppm. For less active compounds as illustrated by the study of Tables V to VIII however, the concentration of active compound in the formulation used may need to be even higher e.g. 500, 1000 or even 2000 ppm.

It is to be emphasised that the exact amount of any particular compound which needs to be added can be readily determined by simple experiment. The amounts recited in this specification are merely by way of illustration only and are not be construed in any limitative sense whatsoever. In more detail, considering certain particularly useful outlets for the active pyrimidine compounds, when used as a seed dressing, for example, the amount of active compound used will depend upon the type of seed being treated, the disease being combatted, the nature of the soil (its pH, organic content and moisture content, for example), climatic conditions prevaling, the time of the year of season, and the type of formulation employed. In general, however, for dressing Barley seed to combat powdery mildew, for example, the amount of composition used is preferably such as to achieve an adhesion to the seed of about 0.08 to 1.0% by weight of the active compound based on the weight of the seed.

A particularly preferred rate is 0.33% by weight. When used as a spray to combat powdery mildew on cucurbits, for example, preferred formulations are those containing from about 5 to 2000 ppm, and preferably from 5 to 500 ppm of active compound, the concentration depending on the volume of spray applied per unit area and the activity of the particular compound. Thus for example the compound 2-dimethylamino-5-n-butyl-4-hydroxy-6-methylpyrimidine may be applied regularly at rates of 50 to 250 rams per hectare to control the disease powdery mildew of melons. When liquid formulations are used to drench the soil surrounding the roots of plants, the formulations may be much more concentrated than those used for spraying the leaves and very long periods of disease control obtained thereby. The amount of formulation used may be such as to provide from about 250 to 500 mg of active compound per plant per season.

We claim:
1. 2-ethylamino-4-methyl-5-n-butyl-6-hydroxypyrimidine and salts thereof.

* * * * *